(12) United States Patent
Khair et al.

(10) Patent No.: US 6,475,153 B1
(45) Date of Patent: Nov. 5, 2002

(54) METHOD FOR OBTAINING BLOOD PRESSURE DATA FROM OPTICAL SENSOR

(75) Inventors: Mohammad Khair, Hoffman Estates, IL (US); Salvador Lopez, Park Ridge, IL (US); Richard Ng, Cary, IL (US); Sanjar Ghaem, Chesapeake, VA (US); William Olson, Lake Villa, IL (US)

(73) Assignee: Motorola Inc., Schaumburg, IL (US)

( * ) Notice: Subject to any disclaimer, the term of this patent is extended or adjusted under 35 U.S.C. 154(b) by 0 days.

(21) Appl. No.: 09/568,781

(22) Filed: May 10, 2000

(51) Int. Cl.$^7$ .................................................. A61B 5/02
(52) U.S. Cl. ....................................................... 600/485
(58) Field of Search ........................... 600/485, 500–503

(56) References Cited

U.S. PATENT DOCUMENTS

| | | | |
|---|---|---|---|
| 3,926,179 A | | 12/1975 | Petzke et al. ............ 128/2.05 N |
| 4,799,491 A | * | 1/1989 | Eckerle ........................ 128/672 |
| 4,802,488 A | | 2/1989 | Eckerle ........................ 128/672 |
| 4,949,710 A | * | 8/1990 | Dorsett et al. ............... 128/680 |
| 5,014,714 A | * | 5/1991 | Millay et al. ................. 128/672 |
| 5,018,529 A | | 5/1991 | Tenerz et al. ................ 128/667 |
| 5,140,990 A | | 8/1992 | Jones et al. .................. 128/665 |
| 5,154,680 A | * | 10/1992 | Drzewiecki et al. ........ 128/672 |
| 5,158,091 A | | 10/1992 | Butterfield et al. .......... 128/672 |
| 5,165,416 A | | 11/1992 | Shinoda et al. .............. 128/672 |
| 5,195,522 A | | 3/1993 | Pytel et al. ................... 128/680 |
| 5,261,412 A | | 11/1993 | Butterfield et al. .......... 128/672 |
| 5,273,046 A | | 12/1993 | Butterfield et al. .......... 128/672 |
| 5,309,916 A | | 5/1994 | Hatschek |
| 5,447,162 A | * | 9/1995 | Shinomiya et al. .......... 128/680 |
| 5,485,848 A | * | 1/1996 | Jackson et al. .............. 128/672 |
| 5,511,554 A | * | 4/1996 | Helfenbein et al. ......... 128/706 |
| 5,724,025 A | * | 3/1998 | Tavori .......................... 340/573 |
| 5,832,924 A | * | 11/1998 | Archibald et al. ........... 128/672 |
| 5,908,027 A | | 6/1999 | Butterfield et al. .......... 128/672 |
| 5,984,874 A | * | 11/1999 | Cerwin ........................ 600/549 |

* cited by examiner

Primary Examiner—Robert L. Nasser
Assistant Examiner—Patricia Mallari
(74) Attorney, Agent, or Firm—Brinks Hofer Gilson Lione

(57) ABSTRACT

An optical sensor generates blood pressure data by obtaining two dimensional images of the surface of the patient's body, such as in the vicinity of the radial artery in the wrist area. Blood flow in the patient causes light to be reflected off a flexible reflective surface applied against the patient with a hold down pressure, and the scattering of light is sensed with a two-dimensional array of photo-detectors. The output of the photo-detectors during systolic and diastolic events is calibrated against known blood pressure measurements taken with a conventional air-cuff sphygmomanometer. Linear calibration relationships between output signal and blood pressure are obtained during calibration for some set of the photo-detectors. When blood pressure data is obtained from the patient, the linear calibration relationship between output signals and blood pressure is applied to the output signals from the set of photo-detectors, resulting in blood pressure data. The method provides for compensation for changes in hold down pressure and translation or rotation of the optical sensor relative to the patient. A preferred optical sensor arrangement for use in performing the method is also described.

52 Claims, 15 Drawing Sheets

METHOD FOR OBTAINING BLOOD PRESSURE DATA FROM OPTICAL SENSOR

CROSS-REFERENCE TO RELATED APPLICATION

This application is related to the patent application filed by the same inventors concurrently herewith, Ser. No. 09/569,586, entitled "OPTICAL NONINVASIVE BLOOD PRESSURE SENSOR AND METHOD," the contents of which are incorporated by reference herein.

BACKGROUND OF THE INVENTION

A. Field of the Invention

This invention relates generally to the field of devices used to measure blood pressure. More particularly, the invention relates to method for continuously obtaining blood pressure data, and related information such as pulse pressure, pulse rate and arterial compliance, from a patient using a non-invasive optical sensor.

B. Statement of Related Art

Non-invasive systems for continuous monitoring of blood pressure, for example during anesthesia, currently exist. Representative patents include the patents to Shinoda et al., U.S. Pat. No. 5,165,416; the patents to Erkele et al., U.S. Pat. No. 4,802,488 and 4,799,491; Jones et al., U.S. Pat. No. 5,140,990, Jackson et al., U.S. Pat. No. 5,485,848 and Pytel et al., U.S. Pat. No. 5,195,522. It is also known to use optical sensors as the means to acquire blood pressure data. See the patents to Butterfield, et al., U.S. Patent 5,908,027; 5,158,091; 5,261,412 and 5,273,046; Cerwin, U.S. Pat. No. 5,984,874 and Tenerz et al., U.S. Pat. No. 5,018,529. The above-referenced patents are incorporated by reference herein.

Prior art mechanical sensors commonly measure blood pressure by detecting transducer changes that are proportional to the detected changes in external force measured at the skin surface during pulsation. These sensors depend on mechanical parts and are therefore more subject to breakdown due to moving parts, and are larger in size thus requiring more space for fitting it on the patient skin. They are typically large in actual size. These sensors employ the use of a single sensor, or an array of sensors from which only one (the one with the highest signal strength) is selected for measurement. Such sensors only cover a small surface area on the skin and are therefore very sensitive to initial exact placement of the sensor on top of the artery. They are also sensitive to movement or minor accidental repositioning. This typically invalidates all calibrations, requiring a need for re-calibrating the system with an air cuff pressure reference. Providing a corrective feedback mechanism for compensating for minor positional changes in sensor placement is not possible due to dependency on a single-point or single-sensor measurement. Furthermore, the resolution of these sensors to blood pressure changes at low level signal strength is not sufficient to obtain accurate results. Other sensors typically require higher hold down pressure (HDP) values in order to obtain a stronger signal due to their low sensitivity. They also offer no corrective feedback mechanism for compensating for minor variations in the hold down pressure, often requiring a need for re-calibration of the sensor at the new hold down pressure value.

Portable oscillometric wrist mounted blood pressure devices also exist, such as the Omron model HEM-609, but these are not intended for continuous blood pressure monitoring. The oscillometric method requires the patient to be at a rested state, and a cuff pressure to be applied by the device that is above the systolic blood pressure of the patient (thus temporarily cutting off circulation in the artery and causing discomfort).

Spacelabs' Modular Digital Telemetry system offers an ambulatory blood pressure (ABP) option for wireless transmission of noninvasive blood pressure data to a central computer, however it is not a tonometric optical blood pressure monitor and it is transmit only.

The above-referenced '027 Butterfield et al. patent describes a device and technique for measuring tonometric blood pressure non-invasively using a one-dimensional optical sensor array. The sensor used in the '027 patent is also described in U.S. Pat. No. 5,158,091 to Butterfield et al. The array detects photo-radiation that is reflected off of a semiconductor, thermally sensitive diaphragm, with the diaphragm deflected in response to arterial pulsation. The diaphragm's thermal properties affect how its surface is deflected. Such thermal properties are associated with calibration coefficients which are used for mapping measured deflections into mmHg blood pressure values. The calibration procedure requires taking such thermal properties into consideration, including a) thermal heating of the diaphragm, b) calibration for optimum vs. non-optimum applanation state of the underlying artery, and c) deformable and a nondeformable portions of the diaphragm so that calibration coefficients can be obtained to map measured sensor output signal into blood pressure.

The present invention is believed to be a substantial improvement over the type of sensors proposed in the prior art. The sensor itself does not depend on thermal considerations. The diaphragm or reflective surface in the present sensor is responsive to any input stress on its surface. Furthermore, a priori knowledge of the exact applanation state is not needed for proper calibration.

Additionally, the sensor is calibrated against a standard conventional air cuff for measuring blood pressure. The calibration procedure automatically compensates for variability that is inherent in patient anatomy and physiological parameters such as body weight, size, skin thickness, arterial depth, arterial wall rigidity and compliance, body fat, etc.. When the sensor is calibrated against known blood pressure (such as using an air-cuff system) all such detailed variables are individually and collectively integrated and linearized in the process of calibrating the sensor. In other words our calibration process is customized to the individual patient anatomy. Accordingly, the sensor and method of the invention produces more accurate results.

The '027 patent describes a set of detectors which are arranged in a single dimensional row. Image processing techniques are not particularly applicable in the format of arrangement of the detectors. In contrast, the sensor and method of the present invention uses a two-dimensional array of photo-sensitve elements which is cabable of producing a digitized two-dimensional image of the underlying skin surface variations due to pulsation. The number and density of elements are significantly higher. Accordingly, the array produces an image that can be processed using image processing techniques, including image transformation algorithms to detect translation or rotation of the sensor. Image processing methods can also be used for filtering, calibrating, tracking, and error-correcting the output of the sensor.

The '027 patent requires a mechanical assembly to provide a means for mechanically pushing the sensor onto the surface of skin tissue, and adjusting the force used for obtaining optimal artery applanation. The present invention does not require the need for such stress-sensing mechanical assembly for proper positioning and adjustment to achieve optimum applanation of the artery. The sensor does require a measurable hold down pressure to be applied on the sensor to produce measurable results for calibration purposes. The hold down pressure can be produced by mounting the sensor to a wrist watch band for example. Furthermore, the sensor and inventive method provide for compensating for changes in the hold down pressure between initial or calibration values of hold down pressure and values of hold down pressure later on when blood pressure data is obtained.

SUMMARY OF THE INVENTION

In a first aspect, a method is provided for obtaining blood pressure data from a patient using an optical blood pressure sensor placed against a patient's body. The sensor includes a two-dimensional array of photo-sensitive elements that obtain image data of the surface of the patient's body. Specifically, the array generates images of the deflection of the patient's body due to arterial blood flow, such as by detection of photo-radiation (i.e., light) reflecting off a flexible reflective surface placed against the patient's body. The scattering patterns are recorded as two-dimensional images. The images are in turn digitized and processed in accordance with the method of the invention.

The method includes a first step of calibrating the optical sensor. A first digitized two-dimensional calibration image of a portion of the patient's body is obtained by the optical sensor, such as the patient's wrist area in the vicinity of the radial artery. While the image is obtained, a blood pressure measurement is made of the patient, such as by using a conventional air-cuff sphygmomanometer. The blood pressure measurement is compared to at least one portion of the first image, such as one photo-sensitive element, or a group of such elements, to thereby obtain a calibration relationship between the selected portion of the first image (i.e., the digitized output signal for photo-sensitive elements corresponding to the selected portion of the image) and the blood pressure measurement. Preferably, a multitude of calibration images are obtained in both systolic and diastolic events, and the comparison between output signal and blood pressure measurement is performed for the set of images. A best fit linear polynomial relationship is found between blood pressure and output signal to thereby arrive at a more accurate calibration relationship.

With the sensor thus calibrated, it is now ready to be used to obtain blood pressure data from the patient. A second digitized two-dimension image of the selected portion of the patient's body is obtained during a period in which the blood pressure data is sought from the patient. The calibration relationship that was derived for the selected portion of the first image (group of one or more photo-sensitive elements) is then applied to a corresponding portion of the second image, namely the set of selected photo-sensitive element or elements. Blood pressure data is thus derived from the application of the calibration relationship to the corresponding portion of the second image. If the blood pressure is the same, the digitized output signal for the selected portion of the calibration and second images would be expected to be the same, and the sensor would therefore report blood pressure data as being the same. If the output signal is different for the second image, linear scaling as provided by the calibration relationship is performed. The blood pressure data is thus derived from the scaled calibration relationship applied to the selected portion of the second image.

The selected portion of the calibration image(s), in the preferred embodiment, comprises a contour or set of locations having substantially the same image intensity values, and the calibration relationship is obtained for the contour. Alternatively, the selected portion of the calibration image could be a single location in said image, that is, a single photo-detector. The calibration relationship is obtained for the single photo-detector. The calibration relationship obtained for the single photo-detector is then applied to the same photo-detector's output in the second image. Alternatively, the selected portion of the calibration image could consist of a set of locations in the first image (i.e., a set of photo-detectors) having substantially different image intensity values. The calibration relationship is obtained for this set of locations and applied to output signals from the set of photo-detectors from the second image and the results averaged to obtain blood pressure data.

The invention also contemplates the ability to compensate for changes in hold down pressure that is applied between the optical sensor and the patient, as such changes could affect the images generated by the array. Thus, the method may further comprise the step of measuring a first hold-down pressure being applied during calibration, measuring a second hold down pressure during the obtaining of the second image, and comparing the first hold down pressure with the second hold down pressure. If the second hold down pressure is substantially different from the first hold down pressure, an error message could be displayed to the user indicating that the sensor cannot obtain valid blood pressure data. If the differences are below a threshold level, a linear scaling may be performed for the blood pressure data (or the calibration relationship) in accordance with the difference between the first and second hold down pressures to arrive at an accurate blood pressure reading. In a preferred embodiment, the hold down pressure measurements are obtained with a strain-gauge type sensor formed as a two-dimensional, flexible membrane or surface that is built into the optical sensor and positioned immediately adjacent to the surface of the patient's body.

In a preferred embodiment, the invention also preferably provides for the ability to compensate for rotation or translation of the optical sensor relative to the patient occurring between the time the calibration image is obtained, and when the second image is obtained. The rotation or translation of the optical sensor can be performed by application of correlation algorithms or other known image analysis techniques to the images generated by the array.

The sensor and inventive method is well suited to an application in which continuous measurements of blood pressure is desired. Thus, a multitude of digitized two-dimensional images can be obtained from the array over a data collection period of time. The frequency at which the images can be generated is a matter of design choice, and will depend on such factors as the readout rate of the sensor, the sampling rate of the electronics, and other factors. The images could be obtained at a rate of say 10 or even 100 per second. The steps of applying the calibration relation to the selected portion of the images and derivation of blood pressure data could be performed for each of the multitude of images, resulting in a continuous stream of blood pressure data. Alternatively, the images could be obtained or processed in a gating window around the period of when the systolic and diastolic events are expected to occur.

The generation of a multitude of digitized two dimensional images enables may useful image processing techniques to be performed on the images. For example, good tracking between measured estimates of blood pressure and actual blood pressure can be achieved by applying a Kalman filter with a one-step predictor. The predicted values can be used to correct for estimation errors, which helps prevent accumulation of error residuals in the reported blood pressure data. As another example, a spatial Finite Impulse Response (FIR) filter can be defined with appropriate coefficients to enhance detection and elimination of motion artifacts and noise, with the FIR filter applied to the multitude of two-dimensional images. As another example, reduction of motion artifacts and noise in sensor output can be obtained by means of application of a one dimensional temporal low pass filter on the output of each individual detector, or a spatial filter that is applied on a group of detectors output, or a spatial and temporal filter applied on multiple detector outputs. Additionally, the output from the detectors can be gated by the heart rate such that computation of end-systolic and end-diastolic pressure values is only considered during a short time-window around the time frame of expected end-systolic and end-diastolic event occurrence. Such timing can be determined and tracked dynamically by means of a Kalman filter, or other simpler methods, as a pulse period can experience an increase or decrease due to tachycardia or bradycardia or general arrythmia. Such gating enables the method to overlook any motion artifacts that might exist in time windows outside the gating window.

The generation of multiple images also allows for other useful physiologic data to be obtained. Arterial compliance can be estimated from a rate of change of skin displacement, which is derived from sequential images. The pulse rate can be derived from sequential images over a measured interval of time. Because of the fact that the sensor detection field spans a full plane of skin area, and because the sensor has a grid of photo-detectors and not just a single sensor, a dynamic image of the movement of a pulse pressure wave in the artery can be constructed. From such a pulse wave, it is possible to extract information such as blood flow rate, which can be measured as the pulse moves across the field of view of the sensor, crossing a known distance in a specific interval of time. Known distance can be determined by known separation between centers of photo-detectors in a grid of a particular detector density and size. The pulse could travel in any direction in the field of view, and the speed of which can be measured independent of its direction. Blood flow rate is then represented as the velocity at which systolic and diastolic events are marked at different points in the sensor field of view.

In another aspect, a method for processing output signals from a two-dimensional array of photo-sensitive elements to generate blood pressure data is provided. The two-dimensional array of photo-sensitive elements is incorporated into an optical blood pressure sensor adapted to be placed on the surface of a patient and obtain optical information as to movement of the patient's skin in response to blood flow. The method comprises the steps of: generating a calibration relationship between output signals from the photo-sensitive elements to known blood pressure measurements, the calibration relationship associated with one or more photo-sensitive elements in the array. Two-dimensional images of the surface of a patient's body are acquired during a period in which blood pressure information is sought for the patient. The images are digitized to thereby obtain a two-dimensional array of digital output values. The calibration relationship is applied to at least a portion of the array of digital output values to thereby derive the blood pressure data.

The methods of the present invention can be used in a variety of sensor designs. A presently preferred sensor assembly is described at length in this document. The sensor includes a housing adapted to be placed adjacent to the patient body, such as at the wrist, and a strap or similar means for applying a hold down force for the sensor in a location where blood pressure data is to be acquired during use of the sensor assembly. The sensor also includes a source of photo-radiation, which in preferred embodiment takes the form of one or more coherent light sources, such as laser diodes. The laser diodes may be arranged in a two dimensional array in one possible embodiment. The sensor also includes a two-dimensional, flexible reflective surface. The reflective surface may take the form of a reflective coating applied to a polymeric membrane. The reflective surface is nominally positioned relative to the radiation source such that the radiation travels in a direction normal to the reflective surface. The reflective surface is placed adjacent to the location on the patient where the blood pressure data is to be acquired, such as against the skin in the wrist area above the radial artery. A hold down pressure sensor, preferably in the form of a strain gauge arranged as a flexible membrane or diaphragm, is also incorporated into the sensor, and placed immediately in contact with the patient and adjacent to the reflective surface.

Radiation from the source is reflected off of the reflective surface onto a two-dimensional array of photo-detectors. The array of photo-detectors is nominally placed in the optical path of the radiation source, but they do not block all the radiation. Rather, they are spaced from one another sufficiently to allow incident radiation from the source to pass in between the detectors and impinge upon the reflective surface at an angle that is normal to the reflective surface. Systolic and diastolic blood pressure fluctuations in the patient are translated into deflections of the patient's skin. These deflections cause corresponding deflections in the two dimensional reflective surface. The associated movement of said flexible reflective surface due to blood pulsation causes scattering patterns from the reflective surface to be detected by the two dimensional array of photo-detectors. After calibration as described herein, these scattering patterns, represented as digital values in a matrix of output values from the sensor as a whole, provide data from which blood pressure data can be extracted. In particular, a linear calibration relationship between blood pressure and output signal is applied to the matrix of output values, or, more typically, one or more of the entries in the matrix corresponding to a portion of the field of view selected for calibration and mapping.

These scattering patterns detected by the array of photo-detectors are processed either in a computing platform in the sensor assembly in accordance with the inventive methods, or alternatively in a remote processing unit such as a base unit. The optical sensor may communicate with the base unit using wireless transmission techniques, or the base unit may be connected to the optical sensor using convention wires or leads in a less preferred embodiment.

The methods of the present invention provide for a calibration relationship that is specific to the patient, and is therefore more accurate than prior art calibration techniques for optical sensors. The methods are completely noninvasive, and offer the ability to obtain blood pressure data and other physiologic data on a continuous basis. In an embodiment in which a wireless transmission technique is used for transmission of digitized image data to a remote base unit, the method offers improvements in patient mobility, convenience, flexibility, and the ability of the base unit to transfer real-time data and various statistical reports to a physician or log physiologic information in a data base for later review.

Further details on these and other features of the invention will be described in the following detailed description of a presently preferred embodiment of the invention.

BRIEF DESCRIPTION OF THE DRAWINGS

A presently preferred embodiment of the invention is described below in conjunction with the appended drawing figures, wherein like reference numerals refer to like elements in the various views, and wherein.

DETAILED DESCRIPTION OF THE PREFERRED EMBODIMENT

Overview

Figure 1:
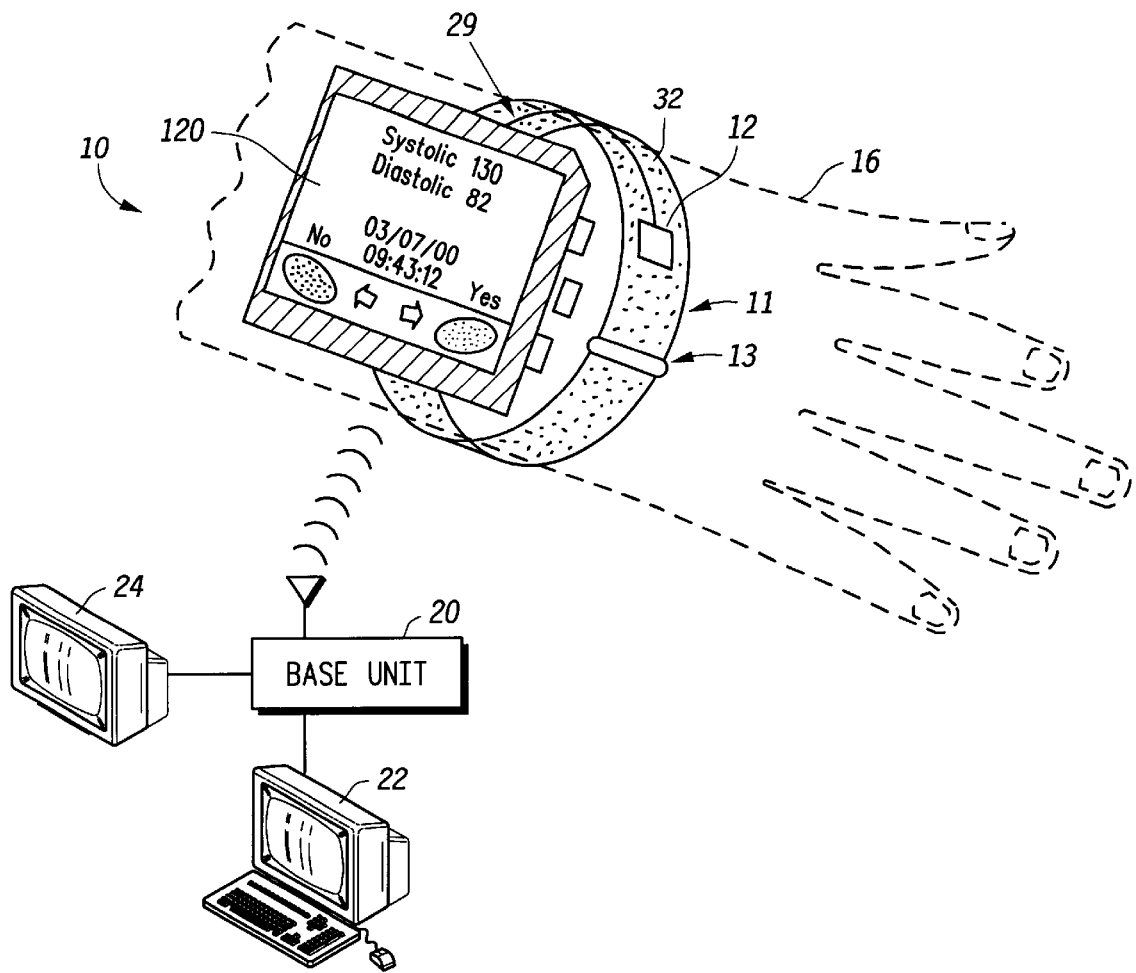
FIG. 1 is a perspective view of an optical sensor for obtaining blood pressure data from a patient in the region of the radial artery at the wrist.
Figure 2:
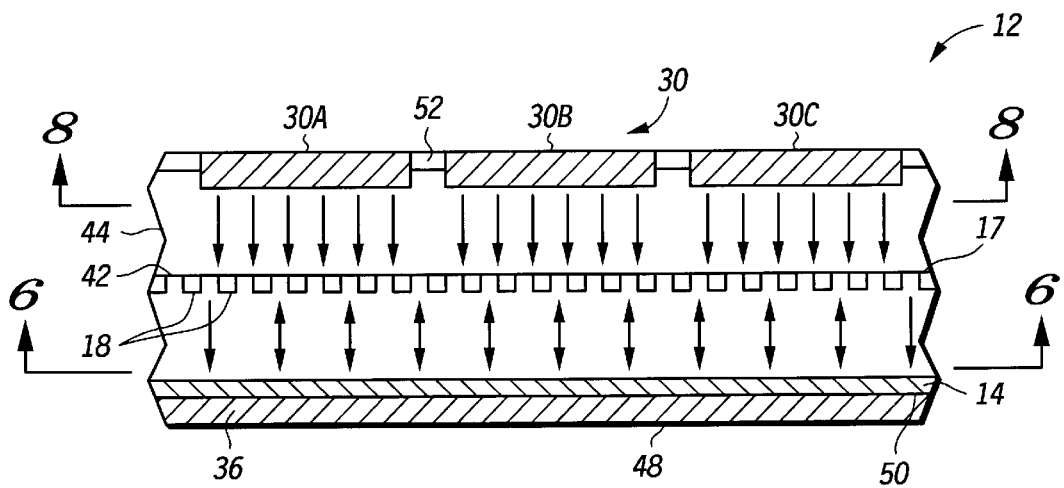
FIG. 2 is a cross-sectional view of the optical sensor of FIG. 1, showing radiation from the light sources in the sensor being directed normal to the reflective surface of the sensor.
Figure 3:
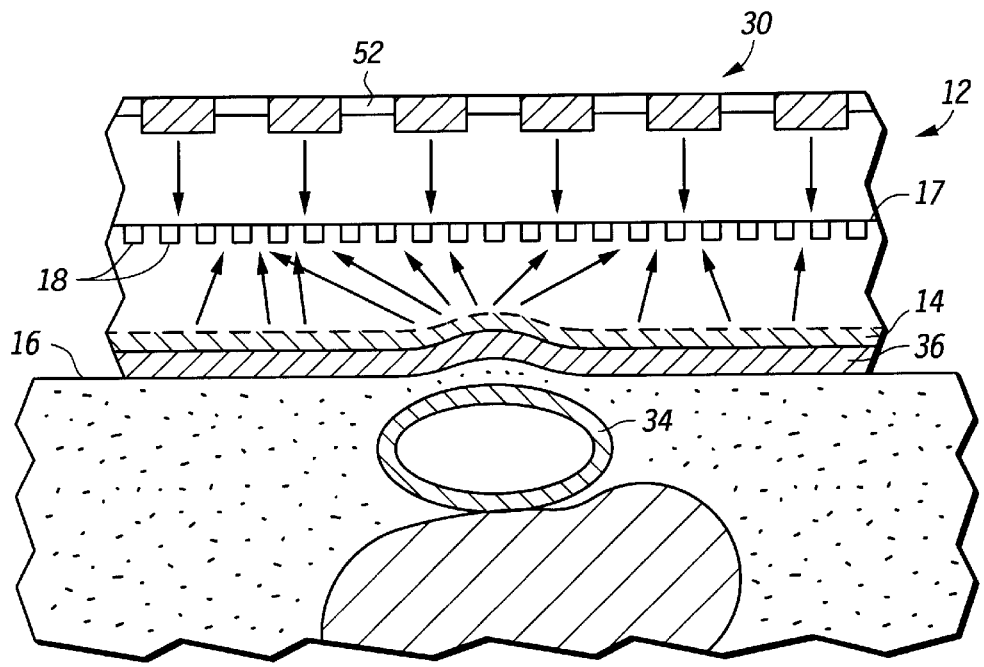
FIG. 3 is a cross-sectional view of the sensor of FIG. 1 shown during use, with skin deflections due to blood pulsation causing the reflective surface in the sensor to scatter light from the radiation sources, with the scattering patterns being detected by the array of photo-sensitive elements in the sensor.

With reference to FIGS. 1–3, a nonivasive blood pressure sensor and data acquisition apparatus for use in the present method invention is shown in FIG. 1. The blood pressure sensor apparatus 10 is suitable for application to a patient's wrist area to acquire blood pressure data. The blood pressure data is acquired via optical techniques described at length herein. In a preferred embodiment, the sensor is capable of wireless bidirectional data communication with a base unit 20, but it can alternatively be constructed as a stand-alone device with a user interface for displaying blood pressure data. In the wireless embodiment, the base unit 20 can be coupled to a computer 22 for display and analysis of blood pressure data or a wireline interface to transmit the data to a remote monitoring station 24.

The sensor apparatus 10, which is mounted to an adjustable, flexible band 11, contains a novel optical sensor arrangement 12 for measuring tonometric blood pressure non-invasively. The sensor's concept of operation is using a light source 30 and light scattering from a reflective surface 14 that is layered against the skin surface 16 to measure blood pressure. The scattering patterns impinge upon a two dimensional array 17 of photo-sensitive elements 18, such as an array of photo-detectors. The array 17 forms a two-dimensional image which is digitized and processed according to techniques described herein to obtain blood pressure data.

Figure 10:
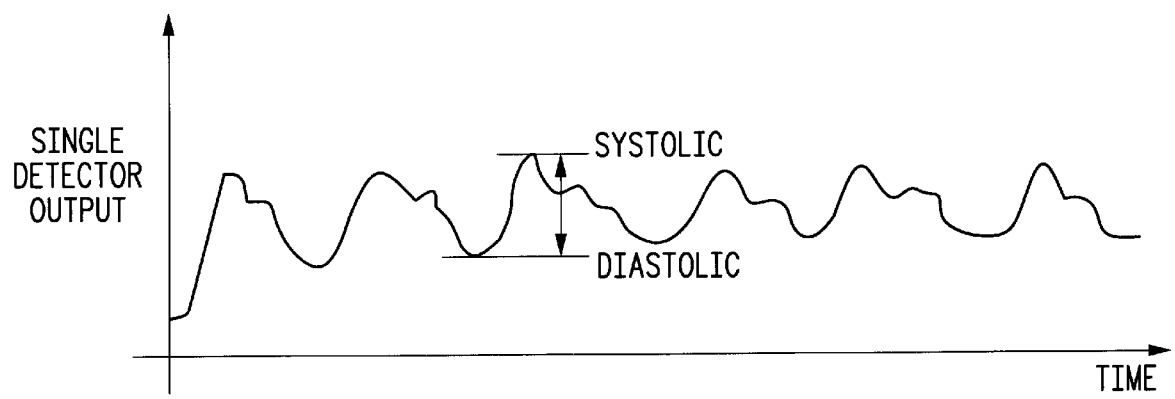
FIG. 10 is a graph of the output of a single detector as function of time, showing the relationship between sensor output and blood pressure value.
Figure 25:
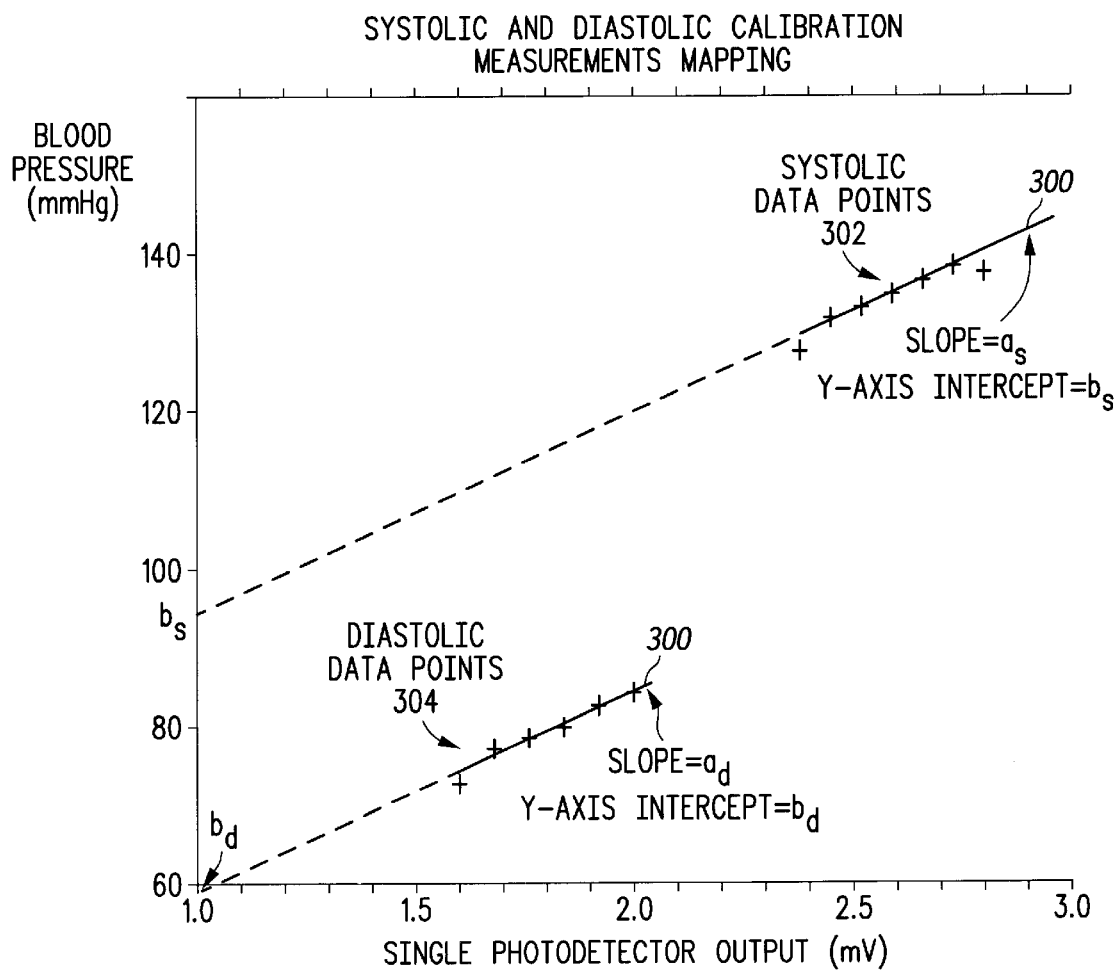
FIG. 25 is a graph of measurements of blood pressure and a single photo-detector output during the systolic and diastolic measurement events.

The sensor 12 is initially calibrated against known blood pressure measurements for the patient, and the calibration relationships between sensor output signals and known blood pressure measurements are used to linearly scale or map output values from the optical sensor to blood pressure data. See FIGS. 10 and 25. Components for the sensor assembly are preferably selected such a linear calibration relationship between sensor output signals and blood pressure in mmHg, at least to a satisfactory level of approximation. This calibration relationship preferably takes the form of the equation:

$$Y^{s,d}(n, m) = a_{n, m}^{s,d} X(n, m) + b_{n,m}^{s,d}, \quad (1)$$

where $Y^{s,d}$ is blood pressure for systolic and diastolic events, (n, m) are one or more individual photo-sensitive elements in an n by m array of such elements, X (n,m) is output signal value (for example, in millivolts for the photo-sensitive element), and $a_{n, m}^{s,d}$ and $b_{n,m}^{s,d}$ are calibration coefficients during systolic and diastolic events for each photo-sensitive element, determined during calibration of the sensor arrangement 10. An example of the calibration data points for systolic and diastolic events for a single photo-sensitive element is shown in FIG. 25 and described subsequently.

The reflective surface 14 is made of a polymeric material coated with a reflective surface that exhibits good localized deformation properties and moisture and thermal insulation against body and environmental moisture and temperature variations so as not to affect its mechanical deformation properties. Suitable materials for the reflective surface are polyimide, polyester, or filled teflon membranes that are coated with a reflective surface. Force from arterial pulsation causes deflections of the skin surface which are measured optically through the reflective scattering of incident rays on the reflective surface 14.

As shown in FIG. 1, the pressure sensor apparatus 10 is attached to the wrist on top of the radial artery. The band 11 includes an adjustment device 13. The sensor includes a light source 30, such as one or more miniature laser diode sources 30 A–F shown in FIG. 2, which emits coherent light that impinges upon the reflective surface 14. The source 30 is oriented relative to the reflective surface 14 such that the direction of propagation of the light is nominally normal to the reflective surface, i.e., when the reflective surface is in a planar attitude with no deflections. If the reflective surface is positioned perfectly perpendicular to direction of propagation, the light beams are reflected vertically and are not scattered into the photo-detectors, as indicated in FIG. 2. The source of radiation could be remotely located and the beam originating from the source conveyed by a light pipe or waveguide 29 (FIG. 1) to the vicinity of the reflective surface 14.

During use, the reflective surface 14 is layered against the skin over the radial artery area in the wrist area with a certain hold down pressure (HDP). Due to the blood pulsations in the radial artery 34 and corresponding skin deflections due to such pulsations, the reflective surface will assume a deflected shape, as shown in FIG. 3, adapting to the local anatomy due to the hold down pressure applied by the sensor's wrist strap 32, as shown in FIG. 1. Scattered reflected light is collected on a ceiling grid of photo-sensitive elements arranged in a two-dimensional array 17, such as an array of 32×32 miniature photo-detectors 18. The light is reflected with a certain pattern that is adapted to the local radial area anatomical surface. Variations in the local surface anatomy due to pulsation are immediately detected as variations in the scattering pattern of the reflected light beams. These variations are detected as fluctuations in the measured power received at the photo-detectors, which provide a direct correlation to the variations of actual blood pressure in the artery in accordance with the calibration relationship of equation (1).

Initial calibration blood pressure values for the sensor are obtained from a conventional air-cuff sphygmomanometer on the arm where the sensor is placed. The systolic and diastolic blood pressure readings can be both measured and entered manually at the base unit or measured electronically by known means and then transmitted digitally to the receiving base unit. A calibration relationship is obtained between the recorded air-cuff systolic and diastolic events and the digitized output signals from the photo-detectors, expressed as equation (1). The output signals from the photo-detectors can therefore be mapped or scaled linearly during subsequent use of the sensor so that photo-detector output represents blood pressure measurements in mmHg. Each photo-detector 18 output represents the average power of the amount of light received at that detector. The higher the density of light received the higher the output signal amplitude produced by the photo-detector. The more scattered or spread the reflected light is, the less dense the light beam and therefore the lower the amplitude of the receiving photo-detector output. Since laser light is incident on the reflective surface in a coherent beam, the reflected beam will have maximum density if the reflective surface is planar. If the reflective surface is deformed, then the incident beam will scatter according to the deformations in the surface. The deformations in the reflective surface will vary dynamically as the skin surface layered against the reflective surface moves due to pulsation of the artery 34 underneath.

In general, more spreading or fanning out of the beam is expected during systolic blood pressure phase than the diastolic phase. This is due to higher vertical deflection or deformation in the skin surface at the systolic event. The difference between the minimum and maximum (delta change) in average power received at each photo-detector at both the systolic and diastolic phases is recorded. The minimum and maximum values of each of these photo-detectors outputs are mapped (by linear scaling) into the corresponding diastolic or systolic blood pressure values (in mmHg) measured during calibration.

Figure 9:
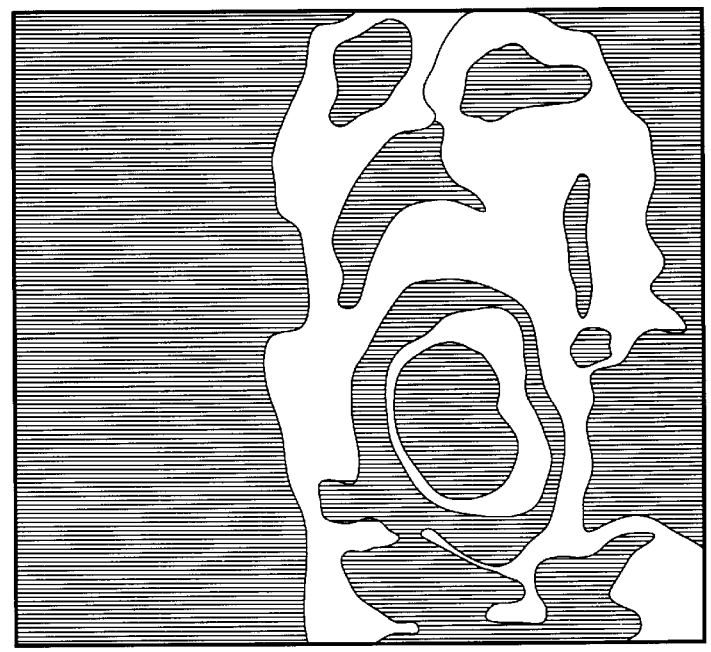
FIG. 9 is a simulation of an image of the surface of the skin that would be obtained by a high resolution photo-detector array.

The overall collective output of the two dimensional array of photo-detectors can be visualized as a two-dimensional image of the activity on the skin surface underneath the sensor, as in the simulated image of FIG. 9. The produced image will contain a pattern produced by the reflected light at the diastolic blood pressure phase that is different from the pattern obtained during the systolic blood pressure phase. This pattern will change dynamically with the pulsation movements of the skin surface. In the illustrated embodiment, the two-dimensional images are generated on a continuous basis, enabling continuous monitoring of the patient's blood pressure.

The sensor also includes a hold down pressure sensor 36 in the form of a strain gauge arranged as a membrane placed below the reflective surface 14. The sensor 36 is used to measure the value of the hold down pressure in terms of resistive change due to strain on that surface. A strain gauge is a resistive elastic sensor whose resistance is a function of applied strain (force). A wire strain gauge is composed of a resistor bonded with an elastic carrier (backing). The backing is applied to the wrist where stress or force could be measured. Many metals can be used to fabricate strain gauges. Typical resistances vary from 100 to several thousand ohms. There are also semiconductive strain gauges, but they are usually quite sensitive to temperature variations. Therefore, interface circuits to these gauges must contain temperature compensation networks. In a preferred embodiment, a hold down pressure interface circuit that connects to the strain gauge could consist of a resistor bias network (such as a Wheatstone bridge circuit) that would translate a hold down pressure to an analog voltage level.

Figure 5:
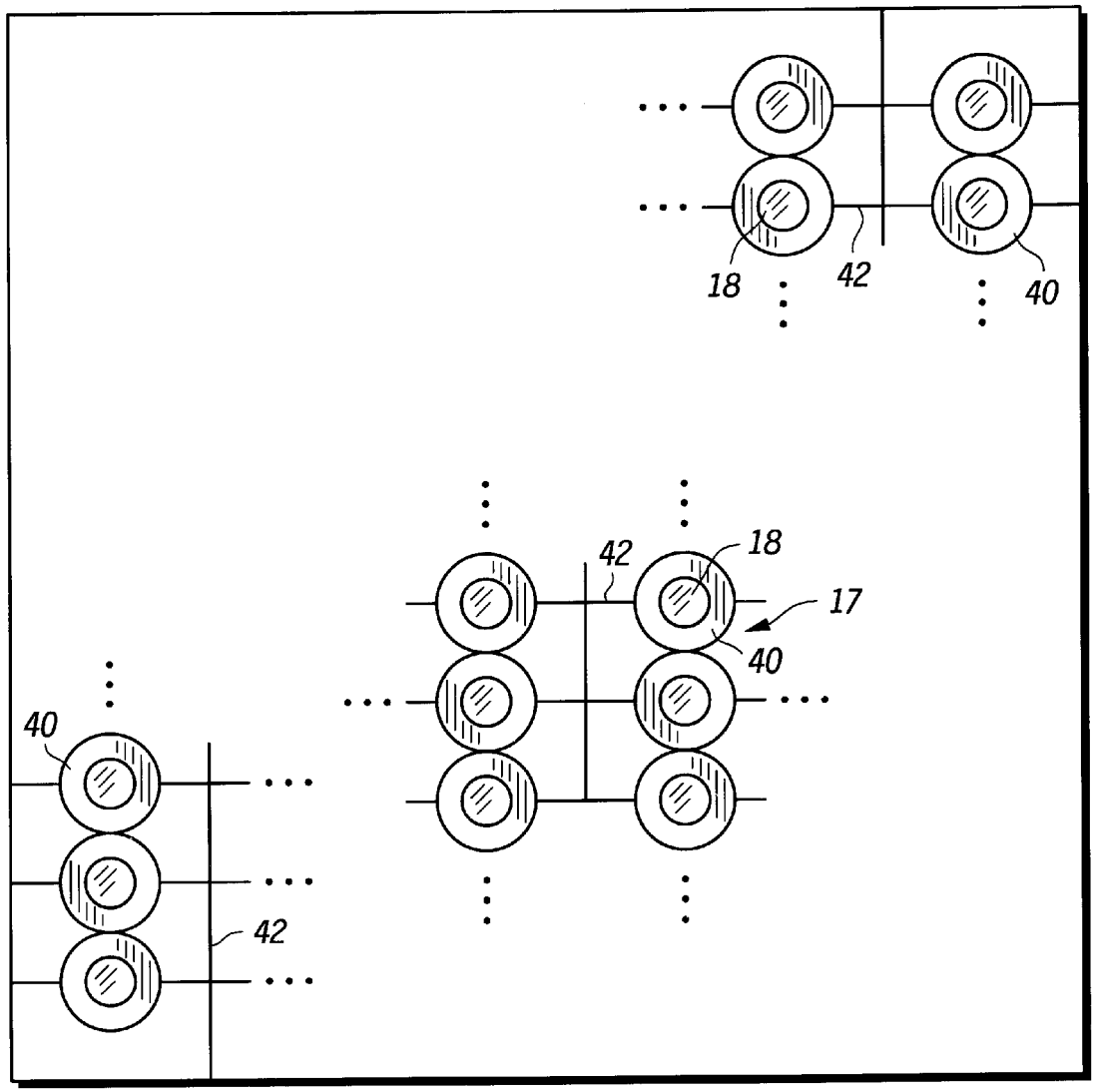
FIG. 5 is a plan view of the array of photo-sensitive elements of FIG. 1 in a presently preferred photo-detector embodiment.
Figure 6:
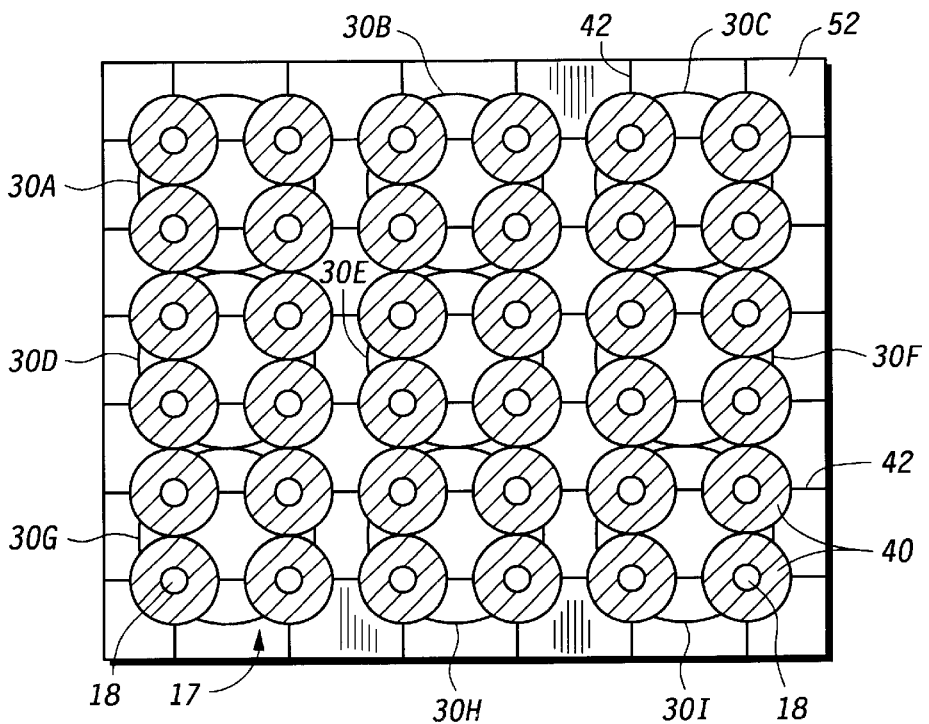
FIG. 6 a plan view of the sensor of FIG. 2 taken along the lines 6—6, with the detector array comprising a 6×6 array of photo-detectors, and the light source comprising a 3×3 array of laser diodes.
Figure 7:
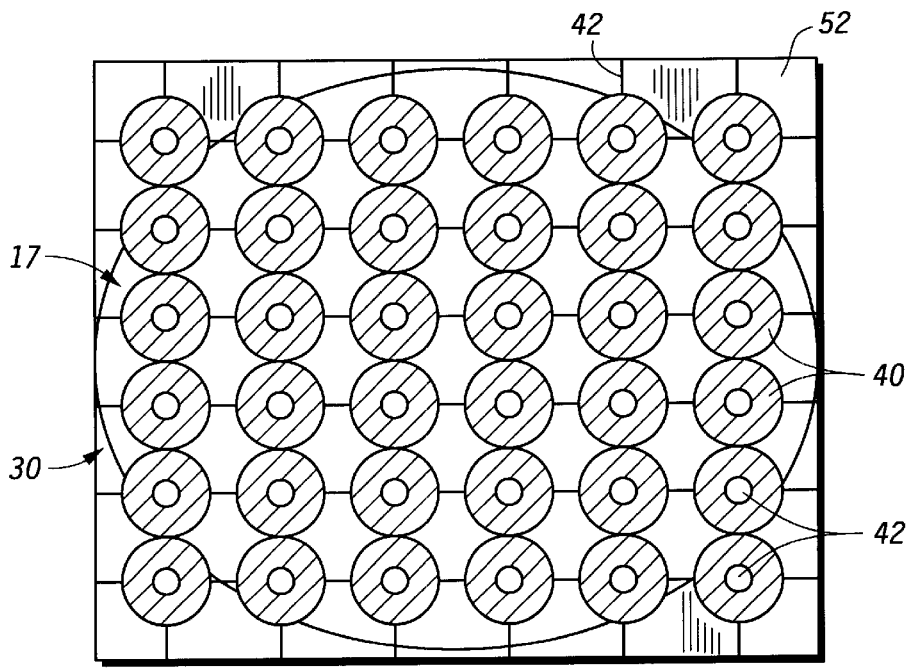
FIG. 7 is a plan view of an alternative arrangement of the sensor, in which a single light source is used in conjunction with a n array of photo-detectors.

The array 17 of photo-detectors can provide a two dimensional image of skin surface topology, such as shown in FIG. 9. Each single photo-detector sensor represents a single pixel in that image. A higher density grid or array of photo-detectors increases the sensitivity of measurements. A preferred embodiment is a 32×32 photo-detector grid density within a 1 $cm^2$ area. This would correspond to a reflective surface having an area of also approximtely 1 $cm^2$ area. As shown in FIGS. 5–7 and explained in further detail subsequently, each photo-detector 18 is positioned in the middle of a black background that blocks light from the emitting source 30. This allows only reflected light to be measured by each photo-detector. Light from the emitting source travels in a direction perpendicular to the reflector surface, as well as cover the whole area of the reflector surface. The diameter of each photo-detector 18 is determined proportionally to selected grid density and desired sensor surface area. There are companies that manufacture custom photo-detector arrays. One such company, Cal Sensor, Inc., of 5460 Skylane Blvd., Santa Rosa Calif. offers custom high density sensor arrays that may be suitable for the instant application.

Figure 4:
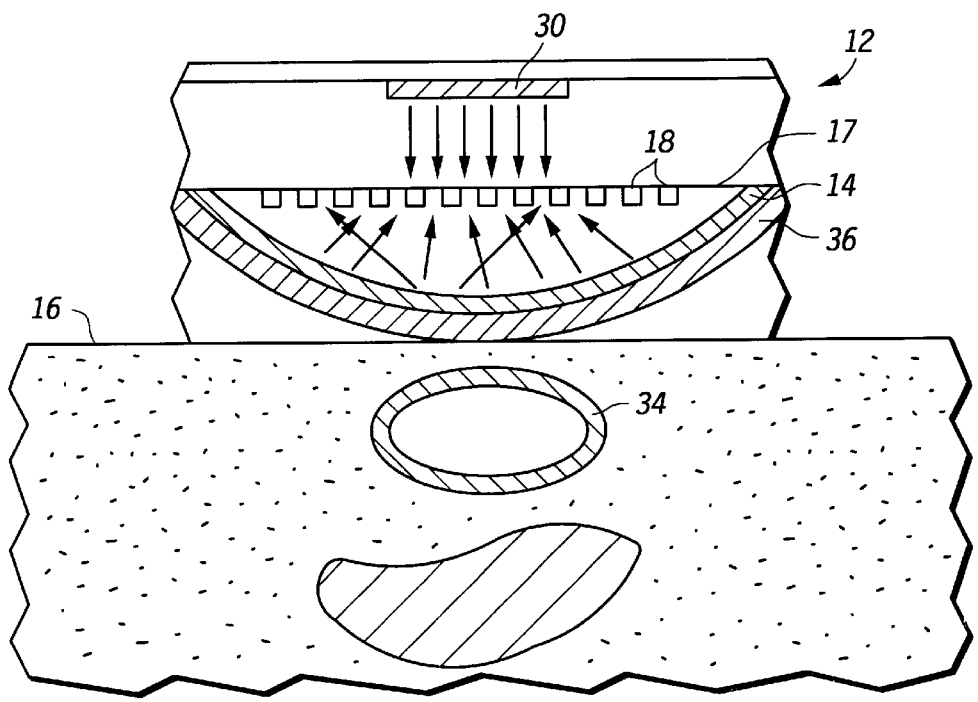
FIG. 4 is a cross-sectional view of an alternative embodiment of the sensor.

As shown in FIG. 4, the reflective surface 14 and HDP sensor 36 could be constructed and arranged in a curved form, such as a parabola, and the calibration and use of the device would proceed as just described.

The present invention also provides a method for obtaining blood pressure data using a blood pressure sensor placed against a patient's body. The sensor includes the two-dimensional array 17 of photo-sensitive elements 18 that obtain image data of the surface of the patient's body. Specifically, the array generates information as to the deflection of the patient's body due to arterial blood flow, such as images, by detecting radiation reflecting off a flexible reflective surface 14 placed against the patient's body. The scattering patterns are recorded electronically as two-dimensional images (or equivalently, as a two dimensional matrix of output values from the individual photo-sensitive elements). The images are in turn digitized and processed in accordance with the method of the invention to arrive at blood pressure readings, as indicated generally in FIG. 10.

The method includes a first step of calibrating the optical sensor 12. The step of calibrating comprises the steps of obtaining a first digitized two-dimensional matrix of output values (e.g., an image) of a portion of the patient's body using the optical sensor, such as the patient's wrist area in the vicinity of the radial artery. Preferably a series of images is obtained during calibration during systolic and diastolic events, and a first order (linear polynomial) best fit routine is applied to the resulting output signals from one or more photosensitive elements to find a first order calibration curve for each photo-detector, and thus the calibration coefficients a $_{n,m}^{s,d}$ and b $_{n,m}^{s,d}$ from equation (1). While the images are being obtained, blood pressure measurements are made of the patient, such as using a conventional air-cuff sphygmomanometer. The blood pressure measurement is compared to at least one portion of the first image, namely one or more photo-sensitive elements 18 in the n×m array 17 of elements, to thereby obtain a calibration relationship between the selected portion of the calibration images (i.e., the digitized output signal for photo-sensitive elements corresponding to the selected portion of the image) and the blood pressure measurement. The calibration relationship may take the form of equation (1) above.

With the sensor thus calibrated, it is now ready to be used to obtain blood pressure data from the patient. A second digitized two-dimensional image (or, equivalently, set of output values from the array) is obtained during a period in which the blood pressure data is sought from the patient. FIG. 9 is a simulation of an image that would be generated with a high resolution embodiment of the array. The image is digitized in the device electronics, described subsequently. The calibration relationship that was derived for the selected portion of the first image (set of photo-detectors) is then applied to a corresponding portion of the second image. Blood pressure data is then derived from the application of the calibration relationship to the corresponding portion of the second image. If the blood pressure is the same, the digitized output signal for the selected portion of the calibration images and the data acquisition images would be expected to be the same, and the sensor would therefore report blood pressure data as being the same. If the output signal is different for the second image, a linear scaling of the calibration relationship is performed using equation (1) and the blood pressure data is derived from the calibration relationship as applied to the output of the selected photo-detectors for the data acquisition image.

The selected portion of the calibration images, in the preferred embodiment, comprises a contour, i.e., a subset of the n×m photosensitive elements, having substantially the same image intensity values, and the calibration relationship is obtained for the contour. Alternatively, the selected portion of the calibration images could be a single location, i.e., and a single photo-detector. The calibration relationship is obtained for the single photo-detector. The calibration relationship obtained for the single photo-detector is then applied to the same photo-detector's output in the data acquisition image. Alternatively, the selected portion of the calibration images could consist of a set of locations, i.e., a subset of photo-detectors, having substantially different image intensity values. The calibration relationship is obtained for this set of locations and applied to output signals from the set of photo-detectors from the second image, with the resulting blood pressure data averaged to arrive at a reported blood pressure.

The optical sensor 12 offers, by nature of its design components, a high sensitivity to variations in blood pressure detected as deformation of the skin surface during pulsation. Each photo-detector acts as a contributing sensor that is providing measurements from a different point of view on the same physical phenomena. The more photodetectors in the grid, or the denser the grid is, the higher the sensitivity of the sensor. A 32×32 array of photo-detectors covering a 1 square centimeter area is considered a representative embodiment, but higher denisities (and thus higher resolution) can be obtained with different array formats, or by using a charge-coupled device. The processing algorithm combines low level signals from all photodetectors to provide collectively a stronger sensitivity and higher resolution for low level measurements.

The mapping of photo-detector outputs into actual blood pressure measurements can be done per individual photo-detector sensor signal basis, or by mathematically combining the signals from multiple photo-detectors. A multi-dimensional signal provides a multi-point sensing mechanism which enables cross-checking and verification of the results from multiple "points-of-view" as seen by a group of photo-detectors. This ultimately provides improved consistency in the reported results, and reduces the probability of error. The availability of a dynamic image that reflects the skin surface topology due to pulsation enables image processing techniques to be used to detect minor sensor position displacements, and respectively adjusting photo-detector calibrations due to such displacements.

As explained above, the processing algorithm maps linearly the measured variations in output from the photo-detectors into blood pressure values. Initial calibration of the sensor with an air-cuff sphygmomanometer generating a known blood pressure measurement provides a linear scaling factor(s) for the peak-to-peak delta difference between systolic to diastolic output of the photo-detector(s). For each photodetector, multiple scaling factors are obtained to describe the linear mapping over many cycles of systolic and diastolic readings during calibration. The multiple scaling factors data is then fitted with a linear polynomial best line fit. When such calibration polynomial scaling factor(s) are applied to each individually corresponding photo-detector output, it will provide a high degree of precision for mapping photodetector readings into actual calibrated blood pressure values. Each photodetector can actually act as an independent blood pressure sensor device, however the combination of multiple detector outputs will provide for a more reliable blood pressure reading. Such multi-point sensor may be useful for validating results for consistency from multiple "points-of-view". The output from each detector can be compared with its nearest neighbor's output to ensure consistency of results, and results that are not reasonable are simply either neglected or averaged out in the process of calculation of mean output diastolic and systolic blood pressure values.

The availability of a multi-point grid of detectors also enables operations to be performed on their combined output, that can yield even more reliable and consistent estimates for actual blood pressure values. A spatial finite impulse response (FIR) filter, for example, can be defined with appropriate coefficients to enhance detection and elimination of motion artifacts or noise. A contour map of grouped photo-detectors with similar output levels during a pulse dynamic event can be generated. Photo-detectors associated with a single contour are connected in a closed loop, and their output can be averaged. Such contours can be further tracked dynamically in time to trace pulsation movements. The output of a full contour of photodetectors, instead of a single detector output, could be used to produce the linear mapping into a blood pressure values.

Since the degree of skin deformation due to pulsation is measured during calibration, exact reproduction of such deformation is expected assuming that all environmental and physiological conditions remain the same. A change in physiological conditions may lower or higher the blood pressure or the pulse pressure (systolic—diastolic) values. This can be tracked as increase or decrease in end-systolic and end-diastolic pressure values. If a major change occurs in a single detector or a contour of detectors' output, that may indicate a displacement such as translation or rotation of the sensor 12 relative to the radial artery site, and thus requires application of sensor position correction. To correct for such displacement, the method optionally provides for computing the values for translation and/or rotation of each image frame to the corresponding image frame acquired during calibration. This can be performed using known correlation, image transformation and/or image processing algorithms. The result is an average estimate of the rotation and translation displacement. The transformation is applied to the calibration scaling factors, resulting in correction for translation or rotational errors.

The sensor 12 design enables changes in hold down pressure (HDP) to be compensated for and therefore more accurate blood pressure values to be obtained. For example, if a reduced end-systolic or end-diastolic pressure value was obtained, it could be due to either a physiological event or a change in the average HDP of the sensor applied to the patient. In the illustrated embodiment, the average sensor HDP on the patients is measured by means of the HDP sensor 36 of FIGS. 2 and 3. Such measurement can be part of the calibration procedure. Minor variations from the calibration HDP value can be compensated for by means of a linear scaling of the blood pressure calibration relationship to obtain a more accurate blood pressure reading.

Figure 11:
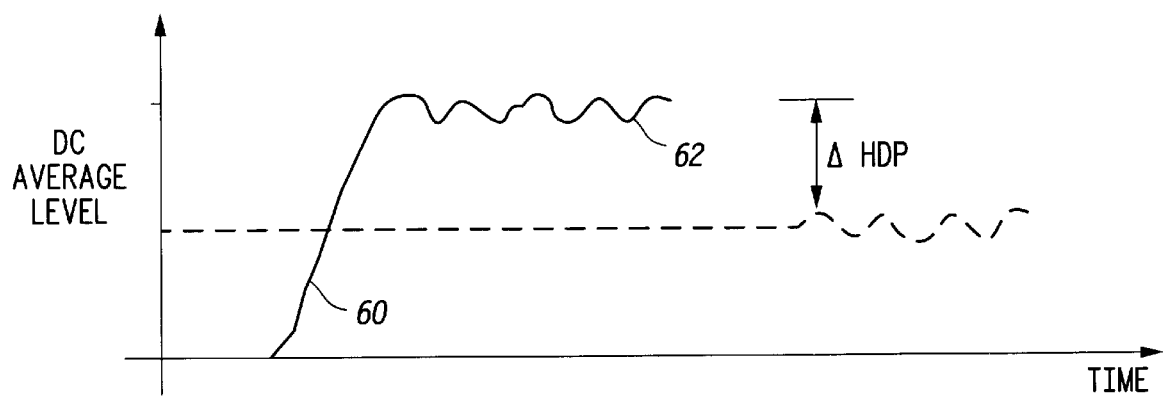
FIG. 11 is a graph of the hold down pressure for the sensor as a function of time.

FIG. 11 is a graph of hold down pressure expressed in terms of DC voltage from the hold down pressure sensor 36 as a function of time. The ramp up 60 indicates the tightening of the wrist strap for the sensor. The oscillation 62 about the average level is due to blood pressure events in the patient during calibration. Deviation from the average hold down pressure during data acquisition phase (as indicated by the dashed lines) will affect sensor output, but this difference ($\Delta HDP_{average}$) can be linearly scaled to the outputs of the photo-detectors to arrive at accurate blood pressure readings. The procedure is explained in further detail below. As shown in FIG. 11, the measured HDP will have a DC component representing overall average HDP, and an AC component representing small variations in HDP due to effect in pulsation. The DC average value of the HDP is used to indicate changes in overall sensor placement force to the skin, thus indicating any motion artifacts or sensor loose attachment or complete detachment from the skin surface.

The optical sensor can provide very high resolution to even faint pulsation movement of the skin due to the nature of the multiplicity of the photo-detectors in the array, and due to the deflection of incident photons in proportion with the reflective surface deformation. No hysteresis effect is experienced by such sensor surface deformation. Also, the higher the density of the photo-detectors in the grid, the higher the sensitivity of the sensor to movement of skin under pulsation.

Sensor Design

Turning now again to the Figures, and in particular to FIGS. 2, 3 and 5–7, the array 17 of photo-detectors 17 of FIG. 2 and 3 is shown in a plan view in FIG. 5. The array 17 of FIG. 5 consists of a 32×32 array of detectors 18, but a higher or lower density of detectors is of course possible. The two dimensional array 17 of photo-detectors preferably comprises an array of at least 36 photo-detectors and is spatially arranged to cover at least one square centimeter in area. An array of 32×32 detectors is a more preferred embodiment with high numbers of detectors increasing cost but resulting in higher resolution and increased sensitivity.

The individual detectors 18 are centered in a black radiation-absorbing background substrate or material 40. Individual columns of detectors are separated from one another by means of a grid or lattice 42, which connects the substrate or material 40 together in both the column and row directions and thereby provide a means for supporting the photo-detectors below the light source 30 of FIGS. 2 and 3. The radiation-absorbing material 40 blocks light from the source 30, thereby only allowing radiation reflected from the reflective surface to impinge upon the photo-detectors. The light source for the photo-detectors is placed behind the lattice 42 and photo-detectors as indicated in FIGS. 2 and 3, with the coherent laser light from the light source passing in between the columns of photo-detectors in the region of the lattice 42, where it travels to reflect off the reflective surface 14.

The assembly of the detectors 18, light source 30, reflective surface 14 and hold down pressure sensor 36 are incorporated into a housing 44 adapted to be placed adjacent to the wrist of the patient. A strap 11 (FIG. 1) provides a hold down force to the sensor assembly. The strain gauge 36 measures the hold down force. The strain gauge 36 is preferably configured as a flexible two-dimensional sheet having a lower surface 48 placed adjacent to the surface of the patient and an upper surface 50 adhered to the lower surface of the reflective surface 14.

Figure 8:
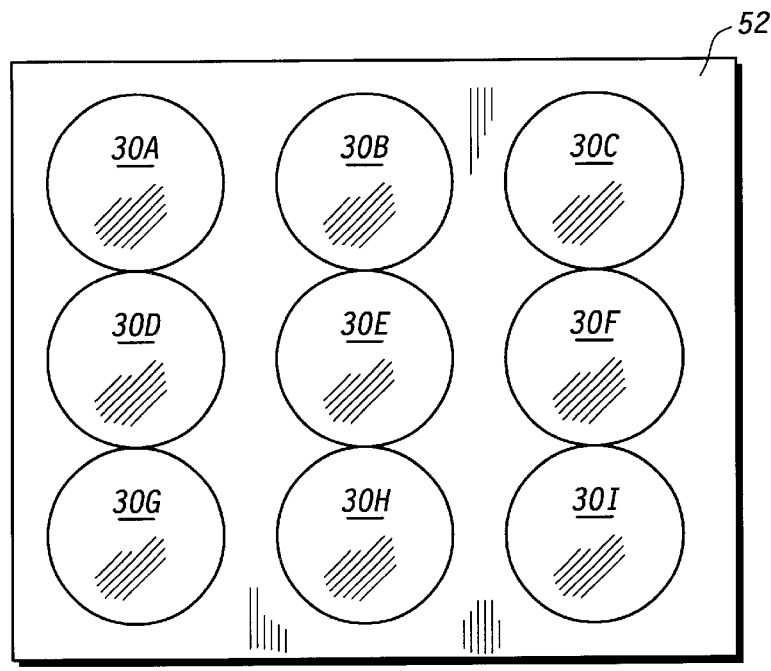
FIG. 8 is a plan view of the array of laser diodes in the embodiment of FIGS. 2 and 6.

FIG. 6 a plan view of the sensor of FIG. 2 taken along the lines 6—6, in which the detector array 17 comprises a 6×6 array of photo-detectors 18. The light source 30 comprises a 3×3 array of laser diodes 30A, 30B, 30C, . . . 30I. Radiation from the light sources 30A–30I passes through the lattice 42 around the periphery of the black radiation absorbing material 40 down onto the reflective surface 14 of FIG. 2 and 3. The light sources are embedded in a suitable substrate 52. As indicated in FIG. 7, the light source could consist of a single large laser diode 30. Alternatively, the light could be remotely located and directed past the lattice 42 by means of a waveguide 29 (FIG. 1) and suitable lenses or other optical system to broaden the beam to the desired width. FIG. 8 is a plan view of the laser diode light sources 30A–I of FIG. 6. Preferably the substrate or mounting material 52 is sufficiently rigid such that the laser diodes remain in a plane such that the light from all the sources 30 travels in a direction that is nominally normal to the reflecting surface. The laser diodes are formed in an array configuration as shown in FIG. 8 and placed in optical alignment with the two dimensional array of photo-detectors, as shown in FIG. 2, 3 and 6.

Figure 12:
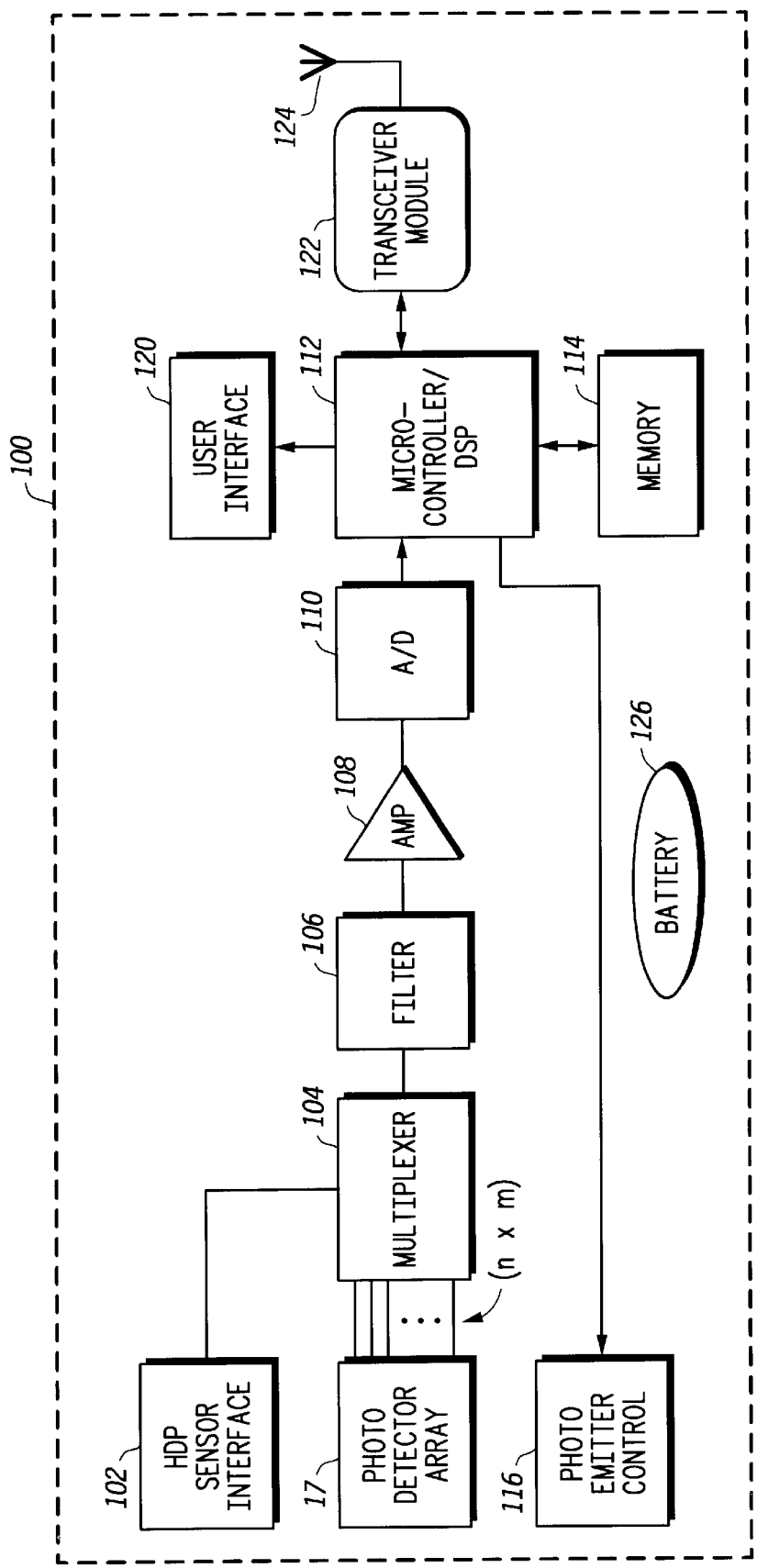
FIG. 12 is a block diagram of the electronics for the sensor of FIG. 2, in an embodiment in which the sensor communicates with a remotely-located base unit using wireless transmission methods.

The scattering patterns acquired by the array 17 could be processed either in the sensor assembly itself and reported by a user interface incorporated in the sensor, or they could be sent to a remote processing unit such as the base unit of FIG. 1 and there processed into useful blood pressure data. FIG. 12 is a block diagram of the electronics for the sensor assembly 12 in an embodiment in which the processing of the data from the sensor is performed either locally or remotely in the base unit. The sensor assembly 12 includes a miniaturized electronics module 100 consisting of a HDP sensor interface 102, and a multiplexer 104 receiving the output signals from the photo-detector array 17. The n×m photodetector analog signals and the HDP sensor signals are multiplexed in multiplexer 104, filtered by an anti-aliasing low pass filter 106, amplified by amp 108, and sampled and converted into digital signals in an analog to digital converter 110.

The digital signals are supplied to a computing platform in the form of a microcontroller and digital signal processor (DSP) unit 112. The microcontroller/DSP performs signal processing of the digital signal supplied by the A/D converter. The signal processing functions include noise filtering and gain control of the digital signal. The microcontroller executes operating system and image processing and calibration routines which are stored in machine-readable form in a memory 114. The memory 114 also stores acquired image data and hold down pressure data from both the calibration phase and the data acquisition phase, and also is used in the HDP and sensor translation and rotation compensation procedures. The microcontroller also issues commands to a photo-emitter control module 116 that controls the illumination of the light source 30 (FIG. 2). The microcontroller presents blood pressure and other physiologic data to the user via a user interface 120, such as a LCD display. Alternatively, the acquired blood pressure data could be transmitted to the base unit using a wireless transceiver module 122 and a low power, miniature RF antenna 124.

The wireless transceiver module 122 may include a buffer, encoder, modulator/demodulator, transmitter, power amp, receiver, filters and an antenna switch, all of which are conventional in the art of wireless communication and omitted for the sake of brevity. A frequency generator is also included in the module 122 that generates a carrier frequency for the RF transmission. The frequency is adjustable by the microcontroller. The microcontroller/DSP controls the frequency generator so as to select a frequency for wireless transmission of data and control messages to the base unit.

A battery 126 with a negative terminal connected to a local ground reference provides DC power to the components.

An embodiment in which the sensor assembly works in conjunction with a wireless base unit can allow the sensor assembly to be remotely managed and configured by the base unit. The wireless arrangement makes possible communications protocols, including command and message procedures, to be employed between the base unit and the wireless sensor. These commands can include start data acquisition commands, data transmission commands, error recovery and retransmission commands, and many others. The patent application of Mohammad Khair, et al., Ser. No. 09/551,719, filed Apr. 18, 2000, which is incorporated by reference herein, sets forth a wireless communication protocol that is particularly well suited for a wireless implementation of the invention.

Base unit

Figure 13:
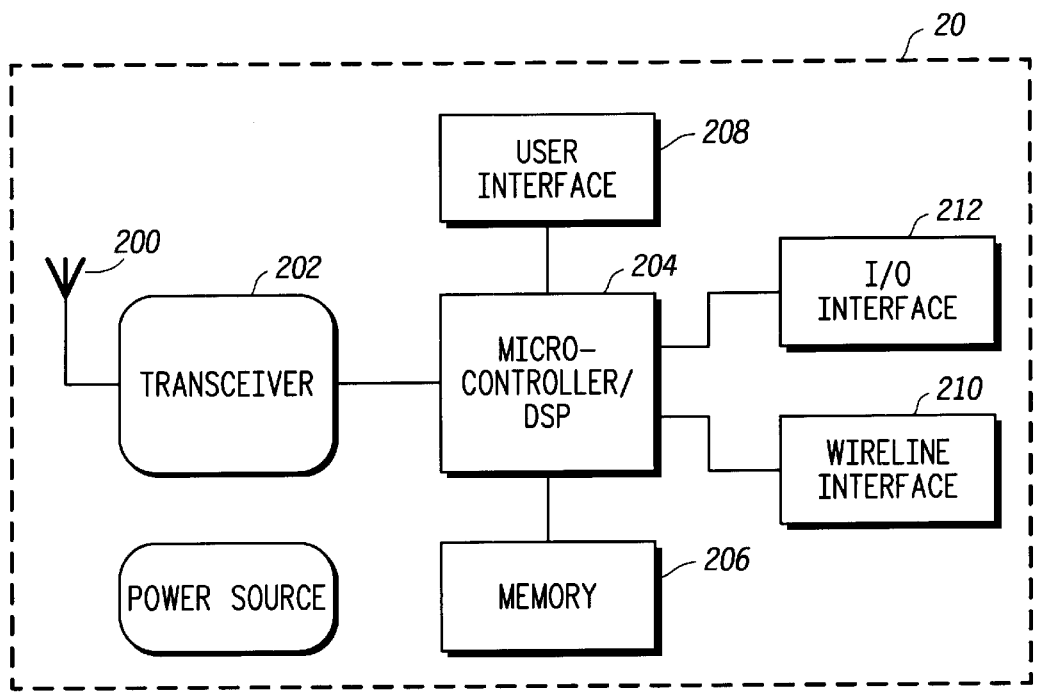
FIG. 13 is a block diagram of a base unit processing sensor data to obtain blood pressure data.

The wireless embodiment of the invention includes the base unit 20 of FIG. 1, which is shown in block-diagram form in FIG. 13. The base unit 20 includes a wireless antenna 200 and transceiver module 202 for two-way RF communication with the sensor apparatus 10. The transceiver module includes a buffer, encoder, modulator/demodulator, transmitter, power amp, receiver, filters and an antenna switch, all of which are conventional in the art of wireless communication and omitted for the sake of brevity. The base unit also includes a microcontroller and DSP computing platform 204 that performs error correction and error diagnosis of the incoming digital communications from the sensor. The microcontroller executes operating system, configuration, transmission management, calibration and data processing routines stored in the memory 206. The microcontroller outputs useful blood pressure and other physiologic data to the user via a user interface 208, or sends it out a wireline interface 210 (such as an RS 232 port) for transmission to a remote location. The base unit also includes an input/output interface 212 for allowing access to the base unit for programming and software downloads by a test or diagnostic machine or an attached computer.

Together, the blood pressure sensor of FIG. 1 and the base unit comprise a noninvasive wireless blood pressure data acquisition system. The sensor has a wireless transceiver for transmitting blood pressure data to the base unit, and receives data acquisition or configuration commands from the base unit. In a preferred embodiment the image processing for calibration and blood pressure data from sensor output signals is performed in the base unit to minimize the cost, size and complexity of the design of the sensor electronics.

Calibration

The calibration of the optical sensor 10 proceeds as follows. First, the blood pressure sensor 12 is placed against the patient's body at a location where blood pressure data is to be obtained. Measurements of the patient's blood pressure are made with a second blood pressure device, such as an air cuff. The hold down force of the optical blood pressure sensor against the patient's body is made by the strain gauge 36. Output signals (i.e., images) are obtained from the array of photo-detectors during systolic and diastolic events, and preferably a multitude of images are obtained. The output signals are calibrated against the measured blood pressure and hold down force data as described herein, to thereby obtain a set of calibration relationships as described in equation (1) for one or more of the photo-detectors. The calibration relationships are stored in a memory, such as in the memory of the sensor or in the memory of the base unit in a wireless embodiment.

Equation (1) is used to linearly map the measured variations in output from the photo-detectors into blood pressure values. Initial calibration with an air-cuff sphygmomanometer provides the linear scaling correlation relationships, namely correlation coefficients $a_{n,m}^{s,d}$ and $b_{n,m}^{s,d}$. For one or more photodetectors, multiple data points are obtained over many cycles of systolic and diastolic readings during calibration. The multiple data points 302 and 304, such as shown in FIG. 25, is then fitted with a first order least-squares polynomial best line fit, represented by the lines 300. Other known methods for best-line fit techniques such as singular value decomposition or weighted least squares fit may be applied. Assume the systolic cuff reading was represented by $Y^s(t)$ and systolic photodetector readings were represented by $X^s(t)$ where t is measurement number taken at a discrete instance in time t=0,1,2,3, . . . , N. N is max number of measurements taken during calibration. Similarly we represent the diastolic cuff reading by $Y^d(t)$ and the diastolic photodetector reading to be $X^d(t)$. Then $Y^s(t) = a_s X^s(t) + b_s$ and $Y^d(t) = a_d X^d(t) + b_d$ where $a_s$ and $a_d$ are respectively the systolic and diastolic scaling multiplication coefficients of a first order least squares polynomial line fit through the multiple calibration measurements, and the $b_s$, and $b_d$ are respectively the systolic and diastolic offset coefficients of the straight line fit equations. The process is repeated for all the n×m detectors, or, alternatively, from some smaller subset of the detectors. The graph of FIG. 25 shows an example for mapping between systolic and diastolic readings between the cuff and a photodetector output. The scaling and offset coefficients are applied through the above equation (1) whenever a conversion from a specific photodetector electrical output in mV into a mmHg is needed.

Method of Operation

Figure 14:
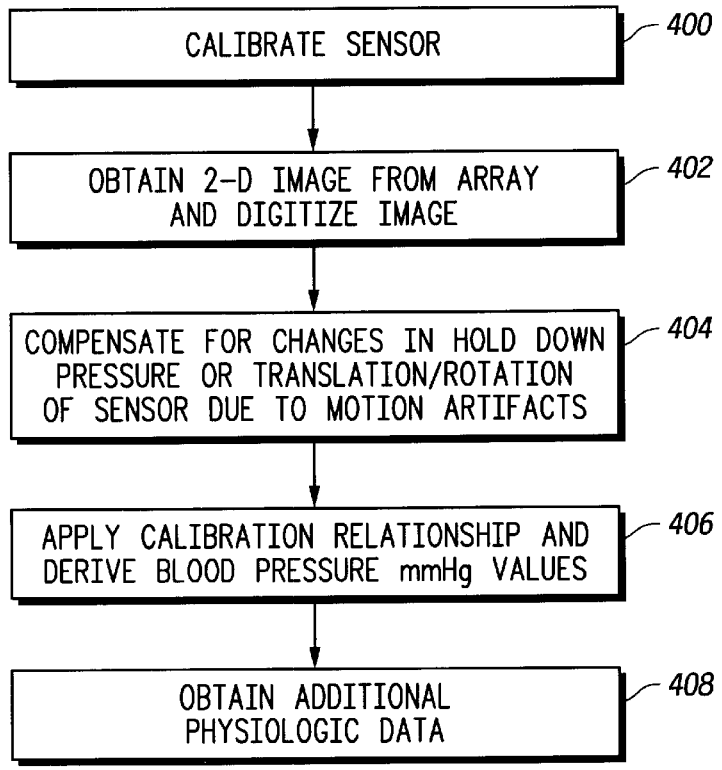
FIG. 14 is a flow chart showing a method by which the optical sensor acquires blood pressure data in accordance with the invention.

The method of operation of the sensor is illustrated in flow chart form in FIG. 14. The method involves the initial calibration of the sensor, step 400, which is described above. Then the sensor is placed on the patient and two-dimensional images in the form of scattering patterns are obtained and digitized, as indicated by step 402. This process preferably is a continuous process. The method continues with an optional step 404 of compensating for changes in hold down pressure or rotation or translation of the sensor relative to the patient's body between calibration and data acquisition. Step 404 may or may not be required depending on the readings from the HDP sensor or drift in sensor output values that indicate that translation or rotation has occurred. At step 406, the calibration relationships from equation (1) are applied to the sensor output to derive blood pressure. At step 408, additional physiologic data such as arterial compliance, pulse rate, etc. is obtained from the sensor. Step 408 is also optional.

Figure 15A:
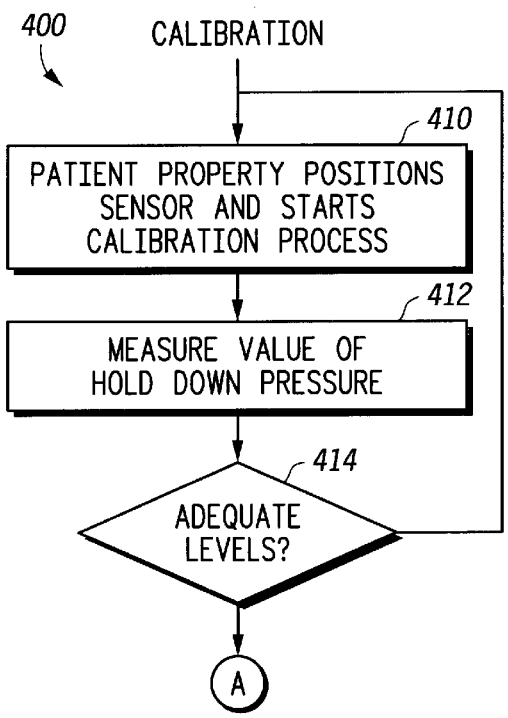
FIGS. 15A and 15B are a flow chart showing the calibration step of FIG. 14 in further detail.
Figure 15B:
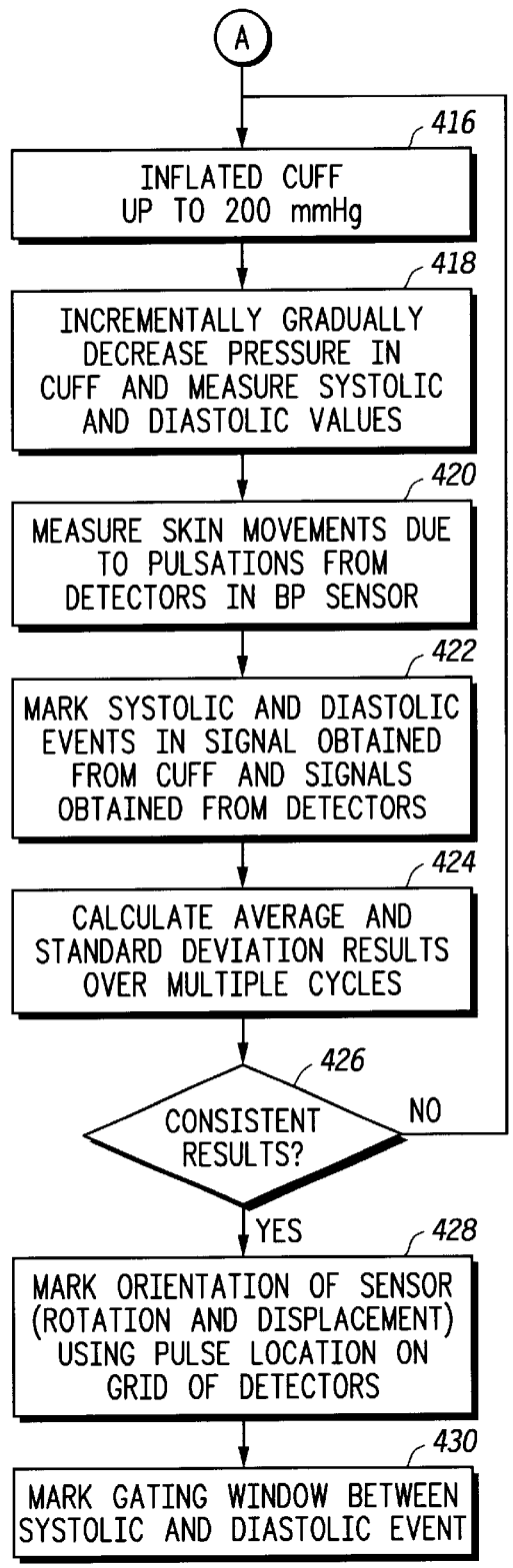

FIGS. 15A and 15B are a flow-chart illustrating the calibration step 400. At step 410, the patient properly positions the sensor on their wrist and starts the calibration process. At step 412, a measurement of the hold down pressure is made with the strain gauge. At 414, a check is made to determine whether the hold down pressure level is adequate. At step 416, the nurse or technician places an air cuff over the patient's arm and inflates the air cuff to 200 mmHg. At step 418, the technician gradually decreases the pressure in the cuff and measures systolic and diastolic values. The values are entered into the base unit via the user interface or alternatively via wireless transmission. At step 420, the blood pressure sensor measures skin movements in the form of scattering patterns due to blood pulsations simultaneously with the measurements of blood pressure, i.e., generates a series of images with the photo-detector array. The images are digitized and stored in memory in the sensor or transmitted to the base unit. At step 422, systolic and diastolic events are marked in the acquired sensor signal and in the air-cuff signal. At step 424, the computing platform in the base unit performs an average and standard deviation of the blood pressure measurements and output signals over multiple cycles. At step 426, the processing routine in the base unit looks to see if the results are consistent, and if not the process goes back to step 416 and repeats.

Figure 24:
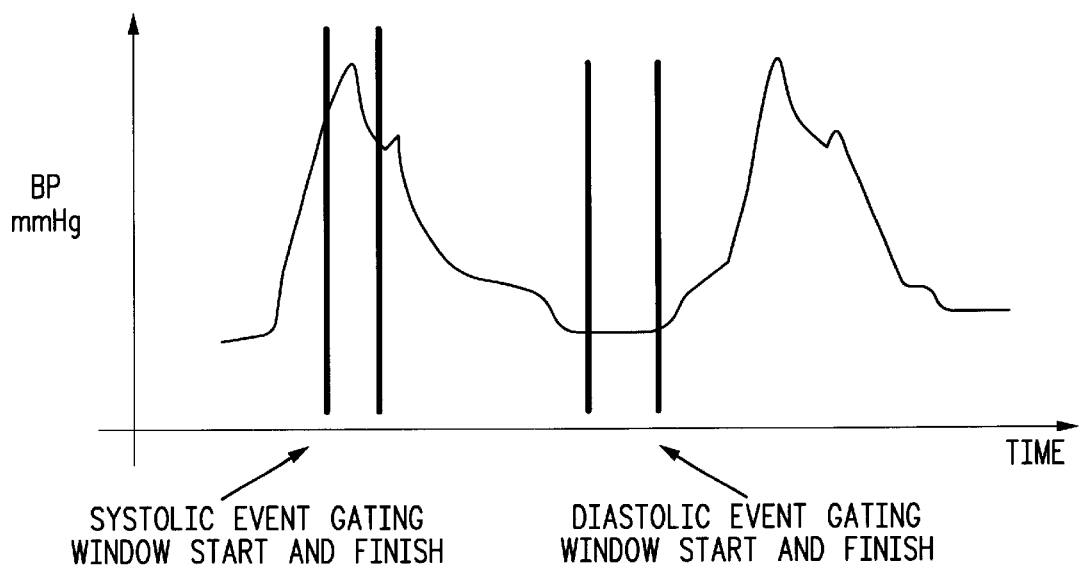
FIG. 24 is a graph of blood pressure in mmHg as a function of time, showing the application of gating windows to measurements of systolic and diastolic pressure.

If the results are consistent, the orientation of the sensor is obtained by processing the output signals from the detectors during calibration to identify the pulse location at step 428. The position is marked, such as by storing a coordinate of the n×m array. Then, a gating window (i.e., temporal duration) for systolic and diastolic events is marked at step 430. The gating window is illustrated in FIG. 24. The gating window is a procedure to obtain systolic and diastolic data during a window of time when the events are expected to occur based on the patient's current heart rate.

Figure 16:
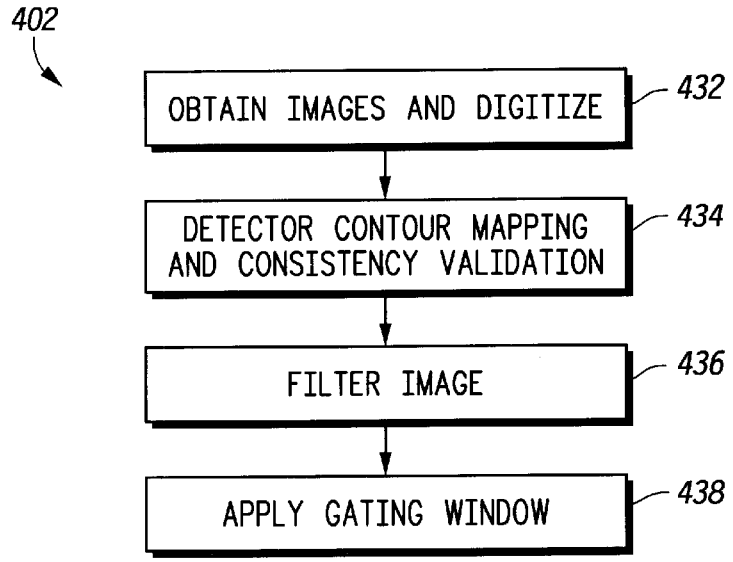
FIG. 16 is a flow chart showing the procedure of obtaining images of FIG. 14 in further detail.

FIG. 16 is a flow-chart illustrating a preferred embodiment of the procedure 402 of obtaining images from FIG. 14 in further detail. In a preferred embodiment the array of photo-detectors generates images at a readout rate of say 10 or 100 per second at step 432. The images are digitized in the sensors. Then, contour mapping is performed at step 434. Basically, the image processing routine in the sensor (or base unit) looks for individual sensor outputs that are substantially the same for any given image, and the set of sensors forms a contour. Several different contours can be thus derived. A consistency validation can then be performed both among and between contour sets to insure that the blood pressure readings are accurate. At step 436, the image is filtered using one or more of a variety of filters, such as Kalman predictor-corrector filter for improved tracking of blood pressure measured estimates with actual pressure, and later optionally applying temporal and/or spatial low pass finite impulse response filters, to produce filtered, smoothed images. Then gating windows are applied at step 438 to the set of collected images to process those images obtained during the gating window.

Figure 17:
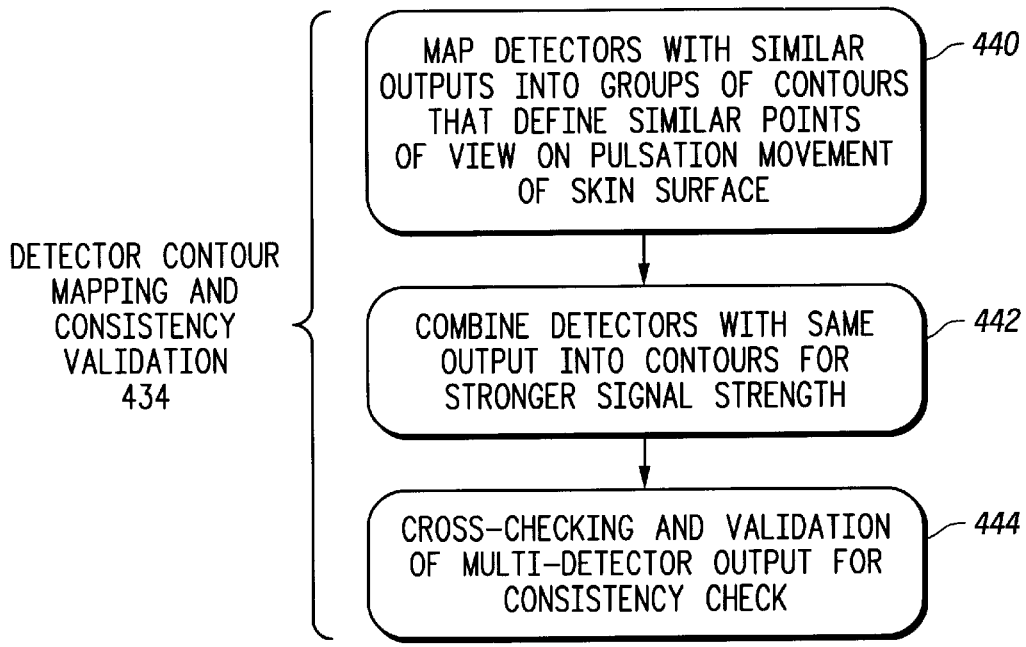
FIG. 17 is a flow chart showing a procedure for detector contour mapping and consistency validation of FIG. 16 in further detail.

The detector contour mapping and consistency validation in step 434 is shown in further detail in FIG. 17. In a first step 440, detectors with similar outputs are mapped or associated into groups of contours, which define similar "points of view" on pulsation movements on the surface of the skin. At step 442, detectors with the same output level are combined into contours to increase the signal strength. At step 444, a cross-checking between contours and validation of multiple photo-detector output is performed for a consistency check or validation.

Figure 18:
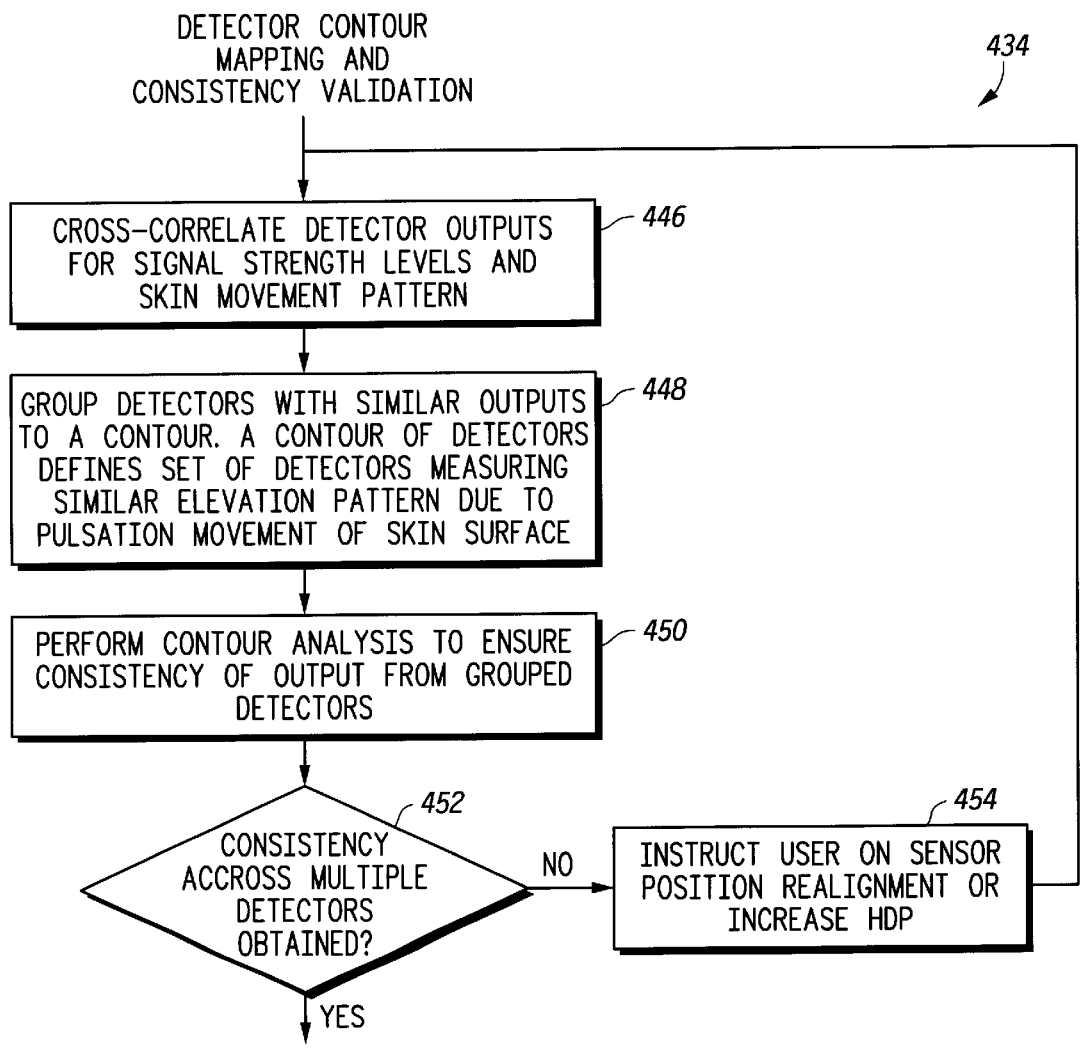
FIG. 18 is another flow chart illustrating the procedure for detector contour mapping and consistency validation of FIG. 16 in further detail.

Another embodiment of the procedure 434 is shown in FIG. 18. In a first step 446, a cross-correlation between detector outputs for signal strength level and skin movement pattern is performed. At step 448, detectors that have similar outputs are grouped into a contour. At step 450, contour analysis is performed to ensure consistency of output from grouped detectors. At step 452, a check is performed of the consistency of the outputs across multiple detectors. If consistency is not obtained, the user is instructed to realign the sensor or adjust the hold down pressure, as indicated at 454. If consistency is obtained, the process proceeds to the filter process 436 of FIG. 16.

Figure 19:
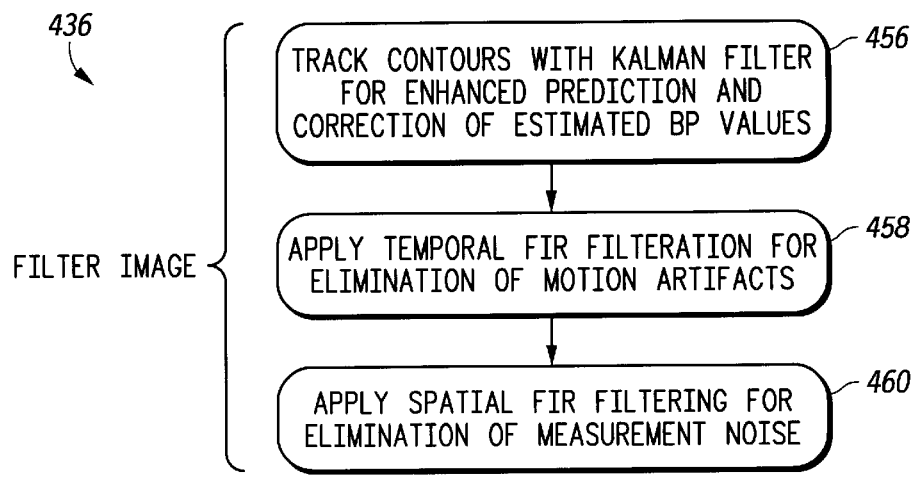
FIG. 19 is a flow chart of the filter image procedure of FIG. 16.

A preferred embodiment of the filter process 436 includes the steps shown in FIG. 19. At step 456, contours are tracked with a Kalman filter for enhanced prediction and correction of estimated blood pressure values. At step 458, a temporal FIR filter is applied to the images to eliminate motion artifacts. At step 460, a spatial FIR filter is applied for elimination of measurement noise. Coefficients for the FIR and Kalman filters can be obtained using known methods.

Reduction of motion artifacts and noise in sensor output can be obtained in two ways: First, by means of application of a filter such as a one dimensional temporal low pass filter applied on the time varying output of each individual detector, or a two-dimensional spatial FIR filter kernel that is applied on a group of detectors output, or a combined spatial and temporal filter applied on multiple detectors output. A two dimensional spatial FIR filter can be applied by defining a filter kernel that is convolved with the image matrix, to produce a new filtered image matrix as a result of the convolution. The direct convolution can be expressed as:

$$Y(n,m) = \Sigma_{k_1} \Sigma_{k_2} h(k_1, k_2) X(n-k_1, m-k_2)$$

where h defines the filter kernel that has support over the region $\{(n,m): 0<=n<N_1, 0<=m<N_2\}$ and $k_1=0$ to $N_1-1$, $k_2=0$ to $N_2-1$.

Figure 20:
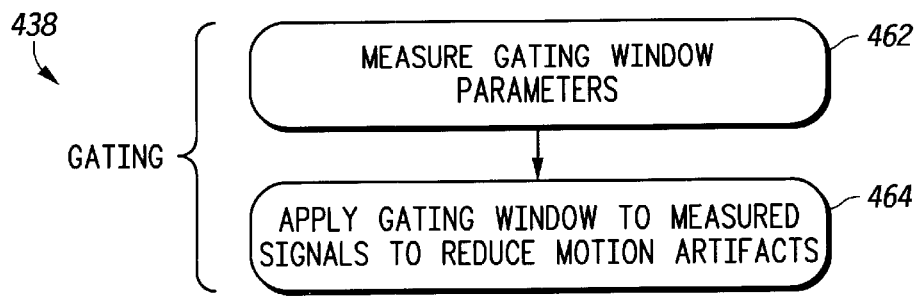
FIG. 20 is a flow chart of the gating procedure of FIG. 16.

The gating window procedure 438 of FIG. 16 is shown in FIG. 20. Basically, gating window parameters, such as frequency and duration of the systolic and diastolic events, are measured at step 462. At step 464, the gating window is applied to the stream of images generated by the array to select images generated during the gating window and thereby reduce motion artifacts that may be occurring outside of the window.

Figure 21:
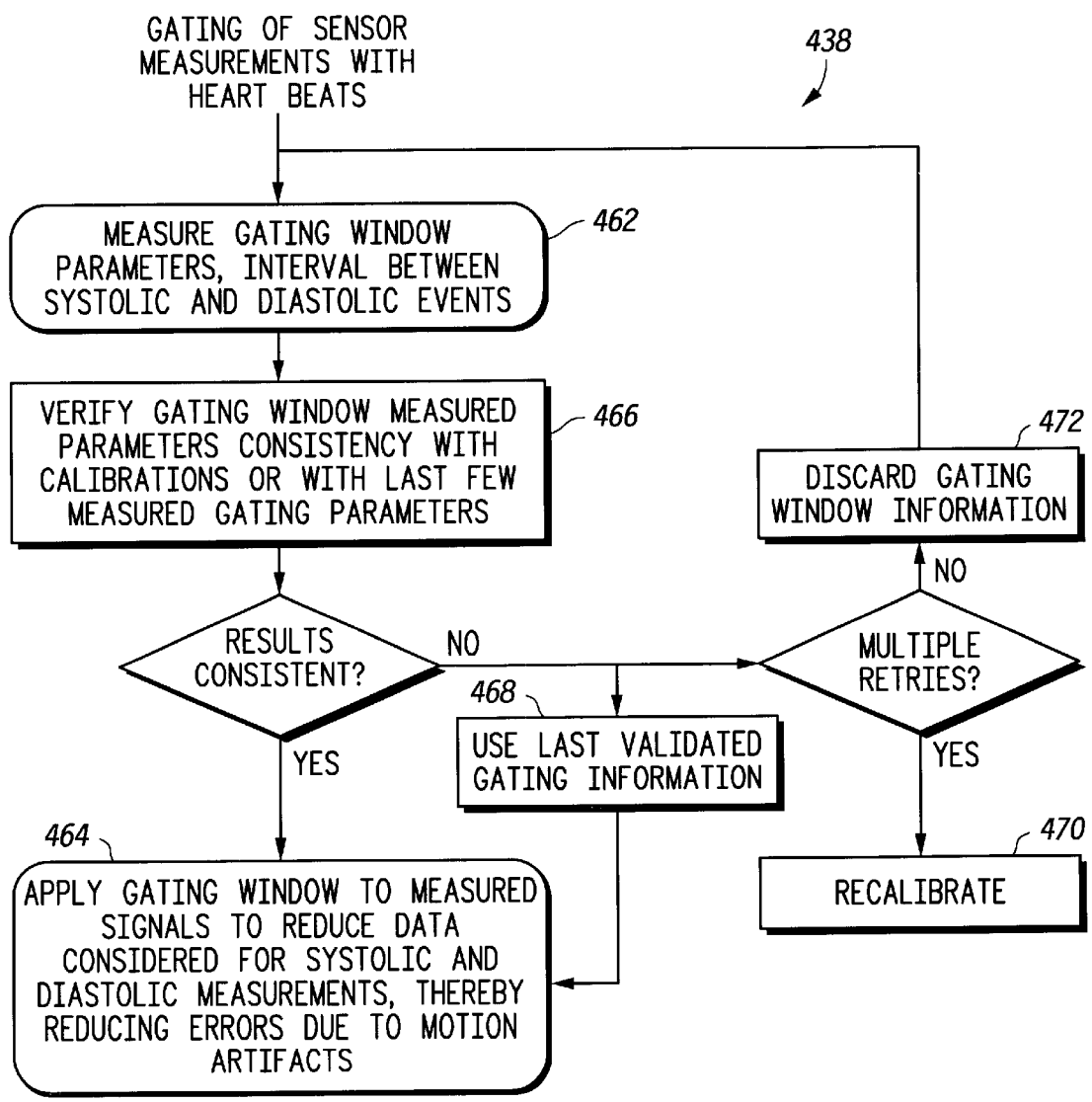
FIG. 21 is a more detailed flow chart of the gating procedure of FIG. 20.

FIG. 21 is a flow chart of an alternative embodiment of the gating window procedure 438. After the measuring gating window parameters (step 462, same as FIG. 20), the gating window parameters are verified for consistency with calibration gating windows, or else with the last few measured gating window parameters, at step 466. If the results are consistent, the process proceeds to the application step 464. If not, the method can either use the last validated gating information at step 468. If there have been multiple retries of the gating window verification and it still has not been verified, the sensor is re-calibrated at step 470. If there have been no previous attempts of window verification, the gating window information is discarded and the process goes back to step 462 as indicated at step 472.

Figure 22:
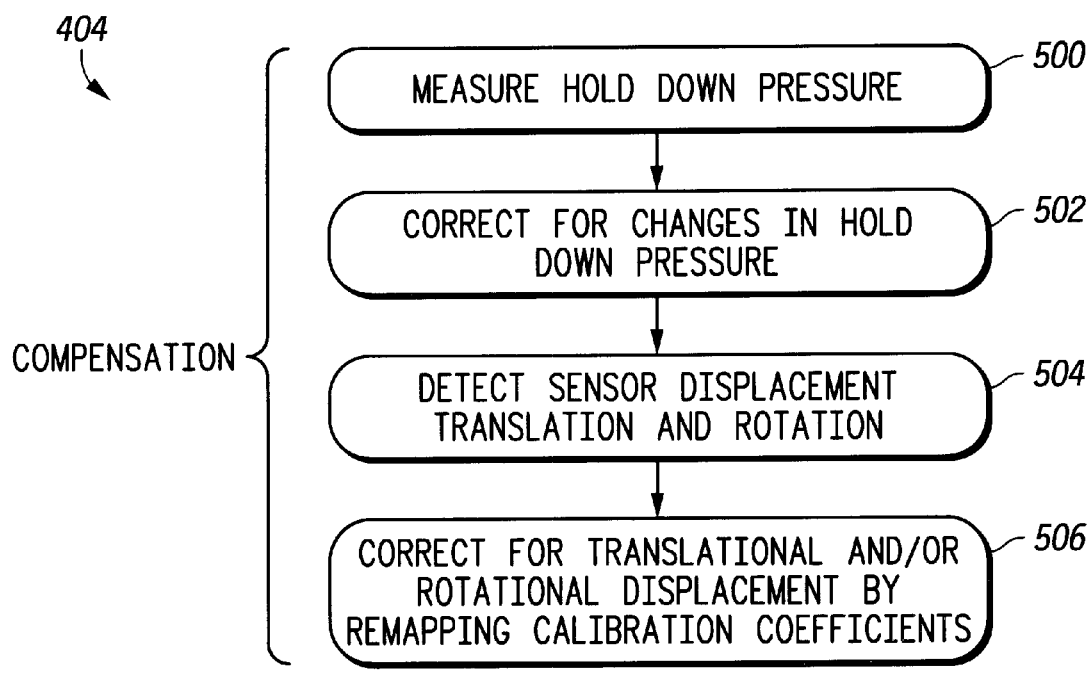
FIG. 22 is a flow chart of the compensation procedure of FIG. 14.

FIG. 22 is a illustration of one form of the compensation step 404 of FIG. 14. First, at step 500 the hold down pressure is obtained while the data is acquired from the sensor. At step 502, changes in the hold down pressure are corrected for by linear scaling of the output of the detectors. At step 506, translation and/or rotational displacement are compensated or by re-mapping calibration coefficients.

This can be tracked as increase or decrease in end-systolic and end-diastolic pressure values. If a major change occurs in a single detector or a contour of detectors' output, that may indicate a displacement of the sensor, and thus requires application of sensor position correction. To correct for such displacement, we can compute the values for translation and/or rotation of each image frame to the corresponding image frame acquired during calibration. The result is an average estimate of the rotation and translation displacement. The transformation is applied to the calibration scaling factors, resulting in correction for error in previously miscalibrated blood pressure values under displacement. The affine transformation between coordinates x,y in one image and u,v in a transformed image can be described as $[x,y,1]=[u,v,1][a_{11} \; a_{12} \; 0,$ so $x=a_{11}u+a_{21}v+a_{31}$ and $y=a12u+a_{22}v+a_{32}.$ $a_{21} \; a_{22} \; 0,$ where $a_{11}=\cos \theta, a_{12}=\sin \theta, a_{21}=-\sin \theta, a_{22}=\cos \theta, a_{31}=T_u, a_{32}=T_v.$ $a_{31} \; a_{32} \; 1]$ The parameters express both a translation transformation with $T_u$, $T_v$, and a rotation transformation of angle $\theta$ expressed as $$[x, y, 1] = [u, v, 1]\begin{bmatrix} 1 & 0 & 0 \\ 0 & 1 & 0 \\ T_u & T_v & 1 \end{bmatrix} \quad [x, y, 1] = [u, v, 1]\begin{bmatrix} \cos\theta & \sin\theta & 0 \\ -\sin\theta & \cos\theta & 0 \\ 0 & 0 & 1 \end{bmatrix}$$

The separation between measured skin deformation, the variable that is mapped into blood pressure values, and the average hold down pressure as an independent variable, enables us to measure and use the average HDP in calculating more accurate blood pressure values. For example, obtaining a reduced end-systolic or end-diastolic pressure values could be due to either a physiological event or a change in the average HDP of the sensor on top of the skin. We can measure the average sensor HDP on the skin by means of the strain gauge located below the reflective surface. Such measurement can be part of the calibration values, and minor variation from calibrated values can be compensated for to obtain more accurate reporting of the estimated blood pressure. The relationship between the average HDP and the photodetector output is again expressed as a linear equation. Such linear equation can be obtained via known method of least squares polynomial line fit of the first order between multiple measured average hold down pressure values vs. corresponding photodetector output values for a specified deformation of the reflective surface. Such relationship can be expressed as $Z(t)=c$ HDP $(t)+d$, where $Z(t)$ represents the output of the photodetector in mV at time t due to HDP(t), with the HDP value taken at measurement time t. The coefficients c, and d represent the scaling and offset factors respectively. For the calibration mapping into mmHg, Y(t) are affected by measured variation in HDP as follows: $Y^s(t)=a_s(X^s(t)+\Delta Z(t))+b_s$, where $\Delta Z(t)=c$ (HDP(t)$_{current}$-HDP$_{calibration}$).

Figure 23:
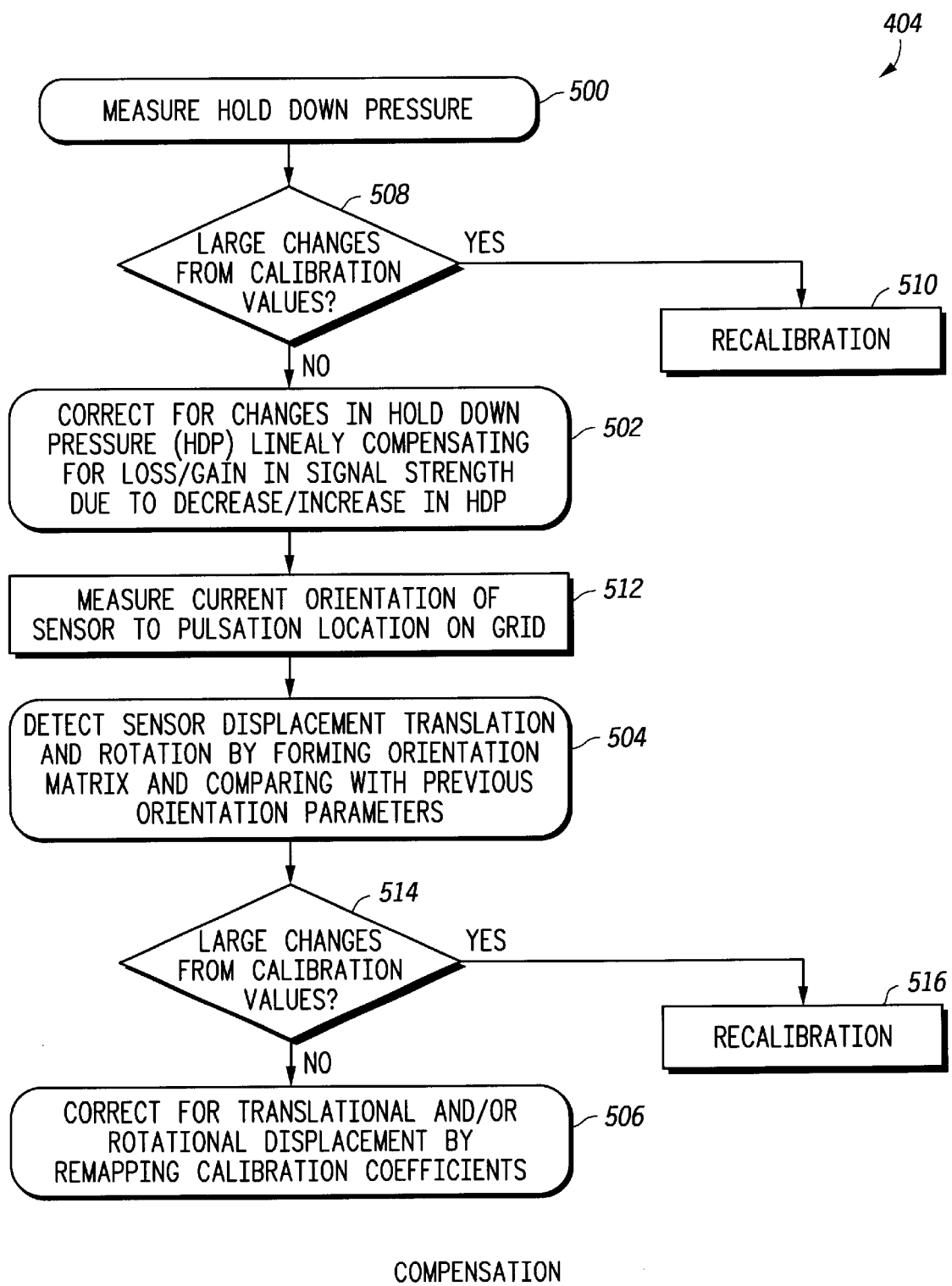
FIG. 23 is a more detailed flow chart of the compensation procedure of FIG. 22.

A modification of the compensation procedure 404 of FIG. 22 is shown in FIG. 23. After hold down pressure is measured, the process looks to see if there are large changes from the calibration values at step 508. If large changes are present, it indicates that the hold down pressure is sufficiently changed that an accurate scaling of output signals to blood pressure data cannot be performed and the user is instructed to re-calibrate the sensor at step 510. Assuming the changes are below a threshold level, the HDP compensation is performed at steps 502. At step 512, the current orientation of the sensor to the location or coordinate of the pulse location during calibration is measured. This can be done using known correlation or image processing methods. From the measurements, the sensor translation and rotation is then determined. If there are large changes from the calibrated orientation at step 514, the calibration is repeated as indicated at 516. Otherwise, the translation or rotation of the sensor relative to the patient is compensated by re-mapping the calibration coefficients.

A windowed-time average can also be applied over multiple pulses to compute average systolic and diastolic blood pressure values. In other words, the average over the last three readings of systolic and diastolic BP values is reported instead of the instantaneous value. That will produce to more consistent results and reduces discontinuities and abnormal variation in reported trends of blood pressure.

Providing good tracking between our measured estimate of blood pressure and the actual blood pressure can be achieved by once more applying a Kalman filter predictor-corrector type. The predicted values from the Kalman filter can be used to correct for potential errors in measurements.

This will help prevent accumulation of residual errors (differences between actual and estimated BP values) in reported blood pressure values. Close tracking is particularly important in continuous monitoring of blood pressure values as such monitoring is performed over extended periods of time.

Use of Sensor to Obtain Additional Physiologic Data

In addition to reporting blood pressure and pulse pressure, arterial compliance can be further evaluated by means of computing the rate of change in skin displacement due to pulsation. Measured detector signals represent displacement of skin in time, or skin movement velocity. The first derivative will yield a skin movement acceleration value, that basically represents the speed of response of artery to input pressure during pulsation. This is directly correlated to the degree of elasticity in the artery being represented.

Because of the fact that the sensor detection field spans a full plane of skin area and because we have a grid of photo-detectors and not just a single sensor, we can construct a dynamic image of flow of pulse pressure wave in the artery. From such a pulse wave, we can extract information such as blood flow rate, which can be measured as the pulse moves across the field of view of the sensor crossing a known distance in a specific interval of time. Such known distance can be deduced by the known separation between photo-detector centers in a photo-detector grid of known photo-detector density and size. The pulse could travel in any direction in the field of view, and the speed of which can be measured independent of its direction. Blood flow rate is then represented as the speed at which systolic and diastolic events are marked at different distant points in the sensor.

Furthermore, the pulse rate can be measured as the rate at which systolic and diastolic events occur per selected interval of time.

Presently preferred embodiments have been described with particularity. Persons skilled in the art will appreciate that modifications and alternative configurations to the optical, electrical and mechanical design of the illustrated embodiments can be made. The true scope of the invention is to be determined by reference to the claims.

We claim:

1. A method for obtaining blood pressure data from a patient using an optical blood pressure sensor placed against a patient's body, said sensor comprising a two-dimensional array of photo-sensitive elements, comprising the steps of:
    (1) calibrating said optical sensor, said step of calibrating comprising the steps of obtaining at least one digitized two-dimensional calibration image of a portion of said patient's body using said optical sensor, substantially simultaneously obtaining a blood pressure measurement form said patient, and comparing said blood pressure measurement to at least one portion of said at least one calibration image to thereby obtain a calibration relationship between said at least one portion of said at least one calibration image and said blood pressure measurement;
    (2) subsequently obtaining a second digitized two-dimensional image of said portion of said patient's body during a period in which said blood pressure data is to be obtained from said patient;
    (3) applying said calibration relationship derived for said at least one portion of said at least one calibration to a corresponding portion of said second image to thereby derive said blood pressure data; and
    (4) performing validation checking of output signals from multiple photosensitive elements corresponding to said portion of said calibration and second two-dimensional images.

2. A method for obtaining blood pressure data from a patient using an optical blood pressure sensor placed against a patient's body, said sensor comprising a two-dimensional array of photo-sensitive elements, comprising the steps of:
    (1) calibrating said optical sensor, said step of calibrating comprising the steps of obtaining at least one digitized two-dimensional calibration image of a portion of said patient's body using said optical sensor, substantially simultaneously obtaining a blood pressure measurement form said patient, and comparing said blood pressure measurement to at least one portion of said at least one calibration image to thereby obtain a calibration relationship between said at least one portion of said at least one calibration image and said blood pressure measurement;
    (2) subsequently obtaining a second digitized two-dimensional image of said portion of said patient's body during a period in which said blood pressure data is to be obtained from said patient;
    (3) applying said calibration relationship derived for said at least one portion of said at least one calibration to a corresponding portion of said second image to thereby derive said blood pressure data;
    (4) generating a multitude of digitized two-dimensional images over a data collection period of time and performing said step (3) for each of said multitude of images; and
    (5) measuring blood flow rate from sequential images in said multitude of two-dimensional images over a measured interval of time.

3. A method for obtaining blood pressure data from a patient using an optical blood pressure sensor placed against a patient's body, said sensor comprising a two-dimensional array of photo-sensitive elements, comprising the steps of:
    (1) calibrating said optical sensor, said step of calibrating comprising the steps of obtaining at least one digitized two-dimensional calibration image of a portion of said patient's body using said optical sensor, substantially simultaneously obtaining a blood pressure measurement form said patient, and comparing said blood pressure measurement to at least one portion of said at least one calibration image to thereby obtain a calibration relationship between said at least one portion of said at least one calibration image and said blood pressure measurement;
    (2) subsequently obtaining a second digitized two-dimensional image of said portion of said patient's body during a period in which said blood pressure data is to be obtained from said patient; and
    (3) applying said calibration relationship derived for said at least one portion of said at least one calibration to a corresponding portion of said second image to thereby derive said blood pressure data;
wherein said portion of said calibration image comprises a single location in said calibration, wherein said calibration relationship is obtained for said single location in said calibration image, and wherein said corresponding portion in said second image comprises said single location in said calibration image.

4. A method for obtaining blood pressure data from a patient using an optical blood pressure sensor placed against a patient's body, said sensor comprising a two-dimensional array of photo-sensitive elements, comprising the steps of:
    (1) calibrating said optical sensor, said step of calibrating comprising the steps of obtaining at least one digitized two-dimensional calibration image of a portion of said patient's body using said optical sensor, substantially simultaneously obtaining a blood pressure measurement form said patient, and comparing said blood pressure measurement to at least one portion of said at least one calibration image to thereby obtain a calibration relationship between said at least one portion of said at least one calibration image and said blood pressure measurement;

(2) subsequently obtaining a second digitized two-dimensional image of said portion of said patient's body during a period in which said blood pressure data is to be obtained from said patient; and (3) applying said calibration relationship derived for said at least one portion of said at least one calibration to a corresponding portion of said second image to thereby derive said blood pressure data;

wherein said portion of said calibration image comprises a set of locations in said calibration image having substantially different image intensity values, and wherein said calibration relationship is performed for said set of locations.

5. A method for processing output signals from a two-dimensional array of photo-sensitive elements to generate blood pressure data, said two-dimensional array of photo-sensitive elements incorporated into an optical blood pressure sensor adapted to be placed on the surface of a patient and obtain optical information as to movement of the patient's body in response to blood flow in the patient, comprising the steps of:

generating a calibration relationship between output signals from a set of at least one of said photo-sensitive elements to known blood pressure measurements;

obtaining, via said optical blood pressure sensor, a two-dimensional image of the surface of a patient's body during a period in which blood pressure information is sought for said patient;

digitizing said two-dimensional image to thereby obtain a two-dimensional array of digital output values, said output values including output values for said set of at least one of said photo-sensitive elements; and applying said calibration relationship to a portion of said array of digital output values corresponding to said set of at least one of said photo-sensitive elements to thereby derive said blood pressure data;

wherein said set of at least one of said photo-sensitive elements comprises a single photo-sensitive element in said array.

6. A method for obtaining blood pressure data from a patient using an optical blood pressure sensor placed against a patient's body, said sensor comprising a two-dimensional array of photo-sensitive elements, comprising the steps of:

(1) calibrating said optical sensor, said step of calibrating comprising the steps of obtaining at least one digitized two-dimensional calibration image of a potion of said patient's body using said optical sensor, substantially simultaneously obtaining a blood pressure measurement form said patient, and comparing said blood pressure measurement to at least one portion of said at least one calibration image to thereby obtain a calibration relationship between said at least one portion of said at least one calibration image and said blood pressure measurement;

(2) subsequently obtaining a second digitized two-dimensional image of said portion of said patient's body during a period in which said blood pressure data is to be obtained from said patient;

(3) applying said calibration relationship derived for said at least one portion of said at least one calibration to a corresponding portion of said second image to thereby derive said blood pressure data; and (4) compensating for rotation or translation of said optical sensor relative to said patient occurring between the obtaining of said calibration and second images.

7. The method of claim 6, wherein said step of compensating comprises the step of applying an algorithm to said calibration and second images to determine a translation or rotation of said at least one portion of said calibration and second two-dimensional images, and generating a new set of calibration relationships according to said translation or rotation.

8. The method of claim 6, wherein said step of compensating is initiated in response to said applying preformed in step (3) in the event that a digitized value of an output signal from a photo-sensitive element corresponding to said at least one portion of said calibration image differs from a digitized value of an output signal from said photo-sensitive element for said second image by a predetermined threshold amount.

9. A method for obtaining blood pressure data from a patient using an optical blood pressure sensor placed against a patient's body, said sensor comprising a two-dimensional array of photo-sensitive elements, comprising the steps of:

(1) calibrating said optical sensor, said step of calibrating comprising the steps of obtaining at least one digitized two-dimensional calibration image of a portion of said patient's body using said optical sensor, substantially simultaneously obtaining a blood pressure measurement form said patient, and comparing said blood pressure measurement to at least one portion of said at least one calibration image to thereby obtain a calibration relationship between said at least one portion of said at least one calibration image and said blood pressure measurement;

(2) subsequently obtaining a second digitized two-dimensional image of said portion of said patient's body during a period in which said blood pressure data is to be obtained from said patient; and (3) applying said calibration relationship derived for said at least one portion of said at least one calibration to a corresponding portion of said second image to thereby derive said blood pressure data;

wherein said portion of said calibration image comprises a set of locations in said calibration image having substantially the same image intensity values, wherein said calibration relationship is obtained for said set of locations.

10. The method of claim 1, further comprising the step of generating a multitude of digitized two-dimensional images over a data collection period of time and performing said step (3) for each of said multitude of images.

11. The method of claim 10, further comprising the step of applying a Kalman filter to said digitized two-dimensional images.

12. The method of claim 10, further comprising the step of applying a finite impulse response filter to at least one of said multitude of two-dimensional images.

13. The method of claim 10, further comprising the steps of measuring gating window parameters and performing said step (3) for said multitude of two-dimensional images obtained during a gating window.

14. The method of claim 10, further comprising the step of estimating arterial compliance from a rate of change of skin displacement determined from sequential images in said multitude of two-dimensional images.

15. The method of claim 10, further comprising the step of measuring pulse rate from sequential images in said multitude of two-dimensional images over a measured interval of time.

16. The method of claim 10, further comprising the step of averaging said blood pressure data from said multitude of two-dimensional images.

17. The method of claim 1, further comprising the step of measuring a first hold-down pressure being applied between said optical sensor and said patient during said calibrating step, measuring a second hold down pressure being applied between said optical sensor and said patient during the obtaining of said second image, comparing said first hold down pressure with said second hold down pressure, and scaling said blood pressure data in accordance with said comparison between said first and second hold down pressures.

18. The method of claim 10, wherein said array comprises a two-dimensional array of photo-detectors detecting scattering patterns from light transmitted from a radiation source nominally oriented normal to the patient's body at said location.

19. The method of claim 18, wherein said light source comprises a source of coherent electromagnetic photo-radiation.

20. The method of claim 1 wherein a computing platform incorporated into said optical pressure sensor performs step (3).

21. The method of claim 1 wherein a computing platform remote from said optical pressure sensor performs step (3).

22. The method of claim 21, wherein said optical blood pressure sensor further comprises a wireless transceiver for sending output data from said array to a remote base unit incorporating said computing platform.

23. The method of claim 22, wherein said remote base unit further comprises a wireless transceiver for sending configuration or data acquisition commands to said optical blood pressure sensor.

24. The method of claim 1, wherein said optical blood pressure sensor further comprises a machine-readable storage medium containing a set of instructions for performing step (3).

25. The method of claim 1, wherein said array comprises a charge-coupled device.

26. The method of claim 1, wherein said sensor is incorporated into a device adapted to be worn around the wrist of a patient.

27. The method of claim 1, wherein said step of calibrating further comprises the steps of making a plurality of blood pressure measurements of said patient during systolic and diastolic events and substantially simultaneously obtaining a plurality of two-dimensional images from said array, and deriving a calibration relationship between said blood pressure measurements and signal outputs from a plurality of photo-sensitive elements in said array from said plurality of two-dimensional images.

28. A method for processing output signals from a two-dimensional array of photo-sensitive elements to generate blood pressure data, said two-dimensional array of photo-sensitive elements incorporated into an optical blood pressure sensor adapted to be placed on the surface of a patient and obtain optical information as to movement of the patient's body in response to blood flow in the patient, comprising the steps of:

generating a calibration relationship between output signals from a set of at least one of said photo-sensitive elements to known blood pressure measurements;

obtaining, via said optical blood pressure sensor, a two-dimensional image of the surface of a patient's body during a period in which blood pressure information is sought for said patient;

digitizing said two-dimensional image to thereby obtain a two-dimensional array of digital output values, said output values including output values for said set of at least one of said photo-sensitive elements; and applying said calibration relationship to a portion of said array of digital output values corresponding to said set of at least one of said photo-sensitive elements to thereby derive said blood pressure data;

wherein said set of at least one of said photo-sensitive elements comprises a set of photo-sensitive elements having substantially similar output signals at said known blood pressure measurement.

29. The method of claim 28, wherein said calibration relationship comprises a linear scaling relationship between blood pressure and a digitized output signal from said set of at least one of said photo-sensitive elements.

30. The method of claim 28 further comprising the step of scaling said blood pressure data in accordance with a change in the hold down pressure applied between said optical sensor and said patient from an initial, calibration hold down pressure and a hold down pressure when said two-dimensional image is obtained.

31. The method of claim 25, wherein said step of generating a calibration relationship comprises the steps of making a plurality of blood pressure measurements of said patient during systolic and diastolic events and substantially simultaneously obtaining a plurality of two-dimensional images from said array, and deriving a calibration relationship between said blood pressure measurements and signal outputs from a plurality of photo-sensitive elements in said array from said plurality of two-dimensional images.

32. The method of claim 1, further comprising incorporating said sensor into a device adapted to be worn around the wrist of a patient.

33. The method of claim 28, further comprising the step of generating a multitude of digitized two-dimensional images over a data collection period of time and performing said steps of digitizing and applying for each of said multitude of images.

34. The method of claim 33, further comprising the step of applying a Kalman filter to said digitized two-dimensional images.

35. The method of claim 33, further comprising the step of applying a finite impulse response filter to at least one of said multitude of two-dimensional images.

36. The method of claim 33, further comprising the steps of measuring gating window parameters and obtaining said multitude of two-dimensional images during a gating window.

37. The method of claim 33, further comprising the step of estimating arterial compliance from a rate of change of skin displacement determined from sequential images in said multitude of two-dimensional images.

38. The method of claim 33, further comprising the step of measuring pulse rate from sequential images in said multitude of two-dimensional images over a measured interval of time.

39. The method of claim 33, further comprising the step of averaging said blood pressure data from data obtained from said multitude of two-dimensional images.

40. The method of claim 28, wherein said array comprises a charge-coupled device.

41. The method of claim 28, wherein said array comprises a two-dimensional array of photo-detectors detecting scattering patterns from light transmitted from a radiation source nominally oriented normal to the patient's body at said location.

42. The method of claim 41, wherein said light source comprises a source of coherent electromagnetic photo-radiation.

43. The method of claim 28, wherein said step of applying is performed by a computing platform incorporated into said optical blood pressure sensor.

44. The method of claim 28, wherein at least one of said step of applying is performed in a computing platform remote from said optical blood pressure sensor.

45. The method of claim 43, wherein said optical blood pressure sensor further comprises a wireless transceiver for sending output data from said array to a remote base unit incorporating said computing platform.

46. The method of claim 45, wherein said optical blood pressure sensor further comprises a wireless transceiver for sending output data from said array to a remote base unit incorporating said computing platform.

47. The method of claim 46, wherein said remote base unit further comprises a wireless transceiver for sending configuration or data acquisition commands to said optical blood pressure sensor.

48. A method for processing output signals from a two-dimensional array of photo-sensitive elements to generate blood pressure data, said two-dimensional array of photo-sensitive elements incorporated into an optical blood pressure sensor adapted to be placed on the surface of a patient and obtain optical information as to movement of the patient's body in response to blood flow in the patient, comprising the steps of:

generating a calibration relationship between output signals from a set of at least one of said photo-sensitive elements to known blood pressure measurements;

obtaining, via said optical blood pressure sensor, a two-dimensional image of the surface of a patient's body during a period in which blood pressure information is sought for said patient;

digitizing said two-dimensional image to thereby obtain a two-dimensional array of digital output values, said output values including output values for said set of at least one of said photo-sensitive elements; and applying said calibration relationship to a portion of said array of digital output values corresponding to said set of at least one of said photo-sensitive elements to thereby derive said blood pressure data;

wherein said calibration relationship comprises a linear scaling relationship between blood pressure and a digitized output signal from said set of at least one of said photo-sensitive elements;

wherein said calibration relationship comprises a plurality of linear scaling relationships between said known blood pressure and a plurality of output signals from a plurality of individual photo-sensitive elements in said array, said linear scaling relationships of the form $y^{s,d}(n, m) = a_{n,m}^{s,d} X(n, m) + b_{n,m}^{s,d}$, where $Y^{s,d}$ is blood pressure for systolic and diastolic events, (n, m) are one or more individual photo-sensitive elements in an n by m array of such elements, X(n, m) is an output signal value and $a_{n,m}^{s,d}$ and $b_{n,m}^{s,d}$ are calibration coefficients during systolic and diastolic events for each photo-sensitive element, determined during calibration of the array.

49. A method for processing output signals from a two-dimensional array of photo-sensitive elements to generate blood pressure data, said two-dimensional array of photo-sensitive elements incorporated into an optical blood pressure sensor adapted to be placed on the surface of a patient and obtain optical information as to movement of the patient's body in response to blood flow in the patient, comprising the steps of:

generating a calibration relationship between output signals from a set of at least one of said photo-sensitive elements to known blood pressure measurements;

obtaining, via said optical blood pressure sensor, a two-dimensional image of the surface of a patient's body during a period in which blood pressure information is sought for said patient;

digitizing said two-dimensional image to thereby obtain a two-dimensional array of digital output values, said output values including output values for said set of at least one of said photo-sensitive elements;

applying said calibration relationship to a portion of said array of digital output values corresponding to said set of at least one of said photo-sensitive elements to thereby derive said blood pressure data; and performing validation checking of output signals from multiple photo-sensitive elements corresponding to said portion of said two-dimensional image.

50. A method for processing output signals from a two-dimensional array of photo-sensitive elements to generate blood pressure data, said two-dimensional array of photo-sensitive elements incorporated into an optical blood pressure sensor adapted to be placed on the surface of a patient and obtain optical information as to movement of the patient's body in response to blood flow in the patient, comprising the steps of:

generating a calibration relationship between output signals from a set of at least one of said photo-sensitive elements to known blood pressure measurements;

obtaining, via said optical blood pressure sensor, a two-dimensional image of the surface of a patient's body during a period in which blood pressure information is sought for said patient;

digitizing said two-dimensional image to thereby obtain a two-dimensional array of digital output values, said output values including output values for said set of at least one of said photo-sensitive elements;

applying said calibration relationship to a portion of said array of digital output values corresponding to said set of at least one of said photo-sensitive elements to thereby derive said blood pressure data;

generating a multitude of digitized two-dimensional images over a data collection period of time and performing said steps of digitizing and applying for each of said multitude of images; and measuring blood flow rate from sequential images in said multitude of two-dimensional images over a measured interval of time.

51. A method for processing output signals from a two-dimensional array of photo-sensitive elements to generate blood pressure data, said two-dimensional array of photo-sensitive elements incorporated into an optical blood pressure sensor adapted to be placed on the surface of a patient and obtain optical information as to movement of the patient's body in response to blood flow in the patient, comprising the steps of:

generating a calibration relationship between output signals from a set of at least one of said photo-sensitive elements to known blood pressure measurements;

obtaining, via said optical blood pressure sensor, a two-dimensional image of the surface of a patient's body during a period in which blood pressure information is sought for said patient;

digitizing said two-dimensional image to thereby obtain a two-dimensional array of digital output values, said output values including output values for said set of at least one of said photo-sensitive elements;

applying said calibration relationship to a portion of said array of digital output values corresponding to said set of at least one of said photo-sensitive elements to thereby derive said blood pressure data; and compensating for rotation or translation of said optical sensor relative to said patient occurring between the obtaining of said calibration relationship and said two-dimensional image.

52. The method of claim 28, further comprising incorporating said sensor into a device adapted to be worn around the wrist of a patient.

* * * * *

UNITED STATES PATENT AND TRADEMARK OFFICE
CERTIFICATE OF CORRECTION

PATENT NO. : 6,475,153 B1
DATED : November 5, 2002
INVENTOR(S) : Khair et al.

It is certified that error appears in the above-identified patent and that said Letters Patent is hereby corrected as shown below:

Column 24,
Line 50, "claim 1" should read -- claim 9 --

Column 25,
Lines 8, 26, 29, 39, 43, 45 and 48, "claim 1" should read -- claim 9 --
Line 18, "claim 10" should read -- claim 9 --

Column 26,
Line 26, "claim 25" should read -- claim 28 --
Line 35, "claim 1" should read -- claim 9 --

Column 27,
Line 13, "claim 43" should read -- claim 44 --
Line 21, "claim 46" should read -- claim 45 --
Line 58, "$y^{s,d}$" should read -- $Y^{s,d}$ --

Signed and Sealed this

Sixth Day of July, 2004

JON W. DUDAS
*Acting Director of the United States Patent and Trademark Office*